United States Patent
Hong et al.

(10) Patent No.: US 9,365,573 B2
(45) Date of Patent: *Jun. 14, 2016

(54) METHOD FOR SYNTHESIZING SAPROPTERIN DIHYDROCHLORIDE

(71) Applicants: ASYMCHEM LABORATORIES (TIANJIN) CO., LTD, Teda Tianjin (CN); ASYMCHEM LIFE SCIENCE (TIANJIN) CO., LTD, Teda Tianjin (CN); TIANJIN ASYMCHEM PHARMACEUTICAL CO., LTD, Teda Tianjin (CN); ASYMCHEM LABORATORIES (FUXIN) CO., LTD, Liaoning (CN); JILIN ASYMCHEM LABORATORIES CO., LTD, Jilin (CN)

(72) Inventors: Hao Hong, Tianjin (CN); James Gage, Tianjin (CN); Chaoyong Chen, Tianjin (CN); Jiangping Lu, Tianjin (CN); Yan Zhou, Tianjin (CN); Shuangyong Liu, Tianjin (CN)

(73) Assignees: ASYMCHEM LABORATORIES (TIANJIN) CO., LTD (CN); ASYMCHEM LIFE SCIENCE (TIANJIN) CO., LTD (CN); ASYMCHEM LABORATORIES (FUXIN) CO., LTD (CN); JILIN ASYMCHEM LABORATORIES CO., LTD (CN); TIANJIN ASYMCHEM PHARMACEUTICAL CO., LTD. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,712

(22) PCT Filed: Dec. 27, 2012

(86) PCT No.: PCT/CN2012/087737
§ 371 (c)(1),
(2) Date: Oct. 10, 2014

(87) PCT Pub. No.: WO2013/152609
PCT Pub. Date: Oct. 17, 2013

(65) Prior Publication Data
US 2015/0105555 A1 Apr. 16, 2015

(30) Foreign Application Priority Data
Apr. 10, 2012 (CN) .......................... 2012 1 0103893

(51) Int. Cl.
| | |
|---|---|
| C07D 475/04 | (2006.01) |
| C07D 239/50 | (2006.01) |
| C07D 239/48 | (2006.01) |
| C07D 239/47 | (2006.01) |
| C07D 303/48 | (2006.01) |
| C07D 317/26 | (2006.01) |
| C07D 317/28 | (2006.01) |
| C07D 317/32 | (2006.01) |
| C07C 209/62 | (2006.01) |
| C07C 221/00 | (2006.01) |
| C07C 225/06 | (2006.01) |
| C07D 301/03 | (2006.01) |
| C07D 301/12 | (2006.01) |
| C07D 301/14 | (2006.01) |

(52) U.S. Cl.
CPC ............ *C07D 475/04* (2013.01); *C07C 221/00* (2013.01); *C07D 239/50* (2013.01); *C07D 301/03* (2013.01); *C07D 301/12* (2013.01); *C07D 301/14* (2013.01); *C07D 317/26* (2013.01); *C07D 317/28* (2013.01); *C07D 317/32* (2013.01)

(58) Field of Classification Search
CPC .. C07D 475/04; C07D 239/50; C07D 239/48; C07D 239/47; C07D 303/48; C07D 317/26; C07D 317/28; C07D 317/32; C07C 209/62; C07C 221/00; C07C 225/06
USPC ......................................................... 544/258
See application file for complete search history.

(56) References Cited

U.S. PATENT DOCUMENTS

| | | | |
|---|---|---|---|
| 2006/0142573 A1 | 6/2006 | Tazawa | |
| 2015/0105555 A1* | 4/2015 | Hong | ............ C07D 475/04 544/258 |

FOREIGN PATENT DOCUMENTS

| | | |
|---|---|---|
| CN | 102627644 A | 8/2012 |
| CN | 102633799 A | 8/2012 |

(Continued)

OTHER PUBLICATIONS

International Search Report PCT/CN2012/087732 filed Dec. 27, 2012; Mail date Apr. 4, 2013.

(Continued)

*Primary Examiner* — Venkataraman Balasubramanian
(74) *Attorney, Agent, or Firm* — Cantor Colburn LLP

(57) ABSTRACT

Disclosed is a method for synthesizing sapropterin dihydrochloride. The present disclosure reduces a synthesis route of the sapropterin dihydrochloride, introduces a chiral center in an asymmetric synthesis manner, in which a tetrahydrofuran solution containing a samarium catalyst is adopted as a catalyst, and obtains a target compound having a high antimer isomerism value by means of selective catalysis. The yield is improved, raw materials are cheap and readily available, and the cost is significantly reduced, hence providing an effective scheme for mass industrial production of the sapropterin dihydrochloride.

11 Claims, 1 Drawing Sheet

(56) References Cited

FOREIGN PATENT DOCUMENTS

| | | |
|---|---|---|
| EP | 0153696 A2 | 2/1985 |
| EP | 0191335 A2 | 8/1986 |
| JP | 574990 A | 1/1982 |
| JP | 60204786 A | 10/1985 |
| WO | 2005063752 A1 | 12/2003 |
| WO | 2009088979 A1 | 7/2009 |

OTHER PUBLICATIONS

U.S. Appl. No. 14/394,079 Connecting via Winsock to STN at stnc.cas.org on port 23; pp. 1-9.

International Search Report for corresponding application PCT/CN2012/087737 filed Dec. 27, 2012; Mail date Apr. 4, 2013.

* cited by examiner

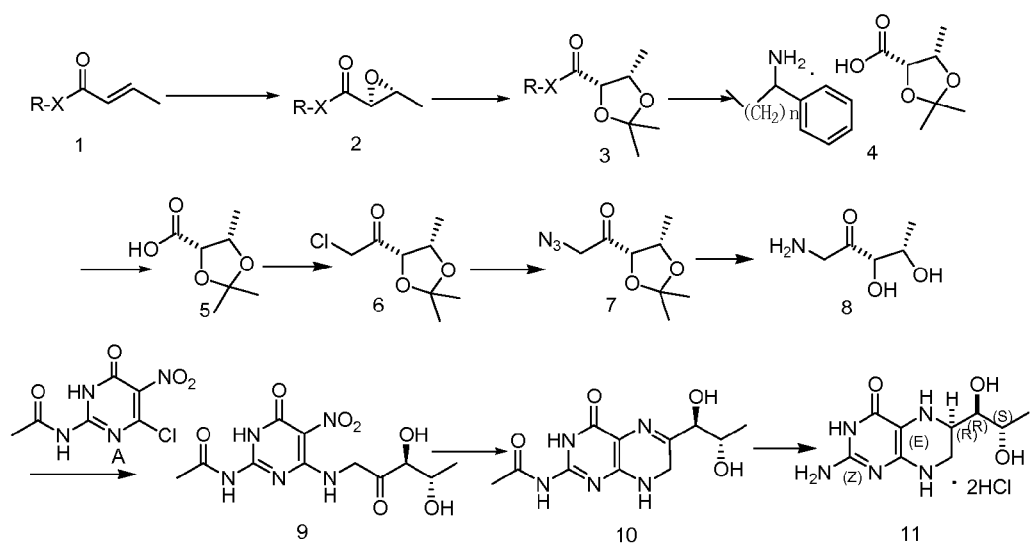

METHOD FOR SYNTHESIZING SAPROPTERIN DIHYDROCHLORIDE

TECHNICAL FIELD

The present disclosure relates to a method for synthesizing a medicine for treating Phenylketonuria (PKU), and particularly to a method for synthesizing sapropterin dihydrochloride.

BACKGROUND

Sapropterin dihydrochloride, chemical name (6R)-2-amino-6-[(1R,2S)-1,2-dihydroxypropyl]-5,6,7,8-tetrahydro-4(1H)-pteridinone dihydrochloride, molecular formula $C_9H_{15}N_5O_3 \cdot 2HCl$, and CAS registry number 69056-38-28, is a synthetic product of tetrahydrobiopterin ($BH_4$) dihydrochloride. $BH_4$ is a cofactor of Phenylalanine Hydroxylase (PAH). Tyrosine is acquired from Phenylalanine (Phe) through hydroxylation under the action of PAH which is low in activity or even inactive in PKU patients, while $BH_4$ is able to activate PAH, promote normal oxidative metabolism of Phe in the bodies of the patients, and reduce the Phe levels in the bodies of some patients. On Dec. 16, 2007, the sapropterin dihydrochloride tablets produced by BioMarin Pharmaceutical Inc. in USA were approved by the Food and Drug Administration (FDA) for marketing for treatment of PKU. Because of the effective activity of sapropterin dihydrochloride, it is extremely necessary to select a route applicable to industrial production with high product purity.

At present, $BH_4$ is mainly synthesized by the following methods reported in literatures:

1. Preparation using 4-hydroxy-2,5,6-triaminopyrimidine (TAP) and 5-deoxy-L-arabinose as raw materials, please see literature E. L. Patterson et al., J. Am. Chem. Soc. 78, 5868 (1956).

2. Preparation using TAP and 5-deoxy-L-arabinose phenylhydrazone as raw materials, please see literature Matsuura et al., Bull. Chem. Soc. Jpn., 48,3767 (1975);

3. Preparation by reaction of raw materials hydroxyl-protected TAP and 4-acetyl-2,3-epoxypentanal through oxidation of iodine and a dehydroxylation protecting group, please see literature Matsuura et al., Chemistry of Organic Synthesis, MI/g. 46. No. 6, P570(1988).

These traditional methods for preparing BH4 have the following major disadvantages: raw materials are expensive, arabinose which can be hardly acquired is used as a carbon atom radical for asymmetric synthesis; there are multiple steps in reactions with low yield, and low product purity, 5-deoxy-L-arabinose is easily degraded in a reaction solution, and products of the synthesis routes above have low stereoselectivity. To sum up, the traditional synthesis methods are not applicable to mass industrial production. Therefore, a synthesis route, which is applicable to industrial production with high product purity, high yield and high stereoselectivity, needs to be searched urgently.

SUMMARY

The present disclosure provides a method for synthesizing a sapropterin dihydrochloride compound. The present disclosure reduces a synthesis route of sapropterin dihydrochloride, introduces a chiral center in an asymmetric synthesis manner, in which a tetrahydrofuran solution containing a samarium catalyst is adopted as a catalyst, and obtains a target compound having a high antimer isomerism value by means of selective catalysis. The yield is improved, raw materials are cheap and readily available, and the cost is significantly reduced, hence providing an effective scheme for mass industrial production of the sapropterin dihydrochloride.

A technical solution of the present disclosure: a method for synthesizing sapropterin dihydrochloride, wherein it includes the following specific steps:

Step 1: add (R)-(+)-1,1'-bi-2-naphthol, triphenylphosphine oxide and a 4 A molecular sieve in the presence of a tetrahydrofuran solution containing a samarium catalyst having a concentration of 5% to 10%, after stirring uniformly, control the system temperature at 0° C. to 25° C., add an oxidant, and add a main raw material compound 1

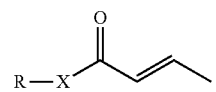

to the system after adding the oxidant, where X=NH or O, R=C1 to C6 alkane or benzyl, react for 20 to 36 hours while preserving the temperature, then add citric acid to the system to stop the reaction, and perform centrifugation, concentration and rectification to obtain compound 2 having a structural formula of

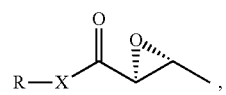

when X is NH, compound 1 is alkyl crotonate or benzamide, and compound 2 is (2S,3R)-2,3 epoxy butanoic acid alkylamido; when X is oxygen, compound 1 is alkyl crotonate or benzyl crotonate and compound 2 is (2S,3R)-2,3 epoxy-alkylbutyrate or (2S,3R)-2,3 epoxy-benzyl butyrate, wherein the molar ratio of

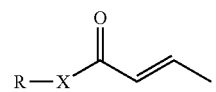

to the samarium catalyst is 1:0.05 to 0.5, the molar ratio of

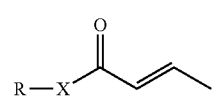

to (R)-(+)-1,1'-bi-2-naphthol is 1:0.05 to 0.5, the molar ratio of

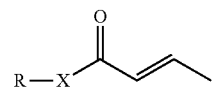

to triphenylphosphine oxide is 1:0.05 to 0.5, the mass ratio of

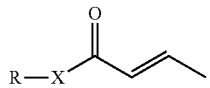

to the 4 A molecular sieve is 1:5 to 15, the molar ratio of

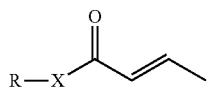

to the oxidant is 1:0.5 to 3, and the molar ratio of

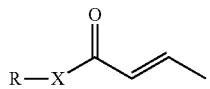

to citric acid is 1:0.05 to 0.5; Step 1 may be also performed according to a method of patent 200910070240.8;

Step 2: add a Lewis acid in the presence of acetone, control the temperature at 10° C. to 30° C., add compound 2, react for 5 to 10 hours while preserving the temperature, add an inorganic base aqueous solution having a concentration of 5% to 10% to the system, and perform liquid separation, extraction and concentration to the system to obtain compound 3 having a structural formula of

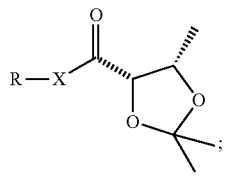

when X is NH, compound 3 is (4S,5S)-2,3-acetonide-alkylbutyramide or (4S,5S)-2,3-acetonide-benzylbutyramide; when X is oxygen, compound 3 is (4S,5S)-2,3-acetonide-alkylbutyrate or (4S,5S)-2,3-acetonide-benzyl butyrate;

wherein the molar ratio of compound 2 to acetone is 1:1 to 4; the molar ratio of compound 2 to the Lewis acid is 1:0.1 to 1; and the molar ratio of compound 2 to the inorganic base is 1:0.5 to 3;

Step 3: add compound 3 in the presence of a polar solvent, increase the temperature to 25° C. to 40° C., add pure water and an alkaline solution, react for 3 to 8 hours while preserving the temperature, perform centrifugation, dissolve a filter cake in a polar solvent which is the same as the polar solvent used in the reaction, add a resolving reagent, preserve the temperature at 15° C. to 30° C. for 3 to 5 hours, perform centrifugation and drying to obtain compound 4, i.e. (4S,5S)-2,3-acetonide-alkylphenylethylamino butyrate having a structural formula of

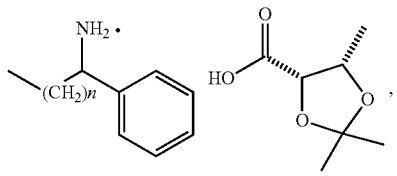

where n=0, 1;

wherein the ratio of the use amount of compound 3 to that of the reaction polar solvent is 1 g/3 to 10 ml; the molar ratio of compound 3 to pure water is 1:0.5 to 3; the molar ratio of compound 3 to an alkaline substance in the alkaline solution is 1:0.5 to 2; the ratio of the use amount of compound 3 to that of the polar solvent for dissolving the filter cake is 1 g/2 to 10 ml; the molar ratio of compound 3 to the resolving reagent is 1:1 to 5;

Step 4: add compound 4 in the presence of an ether solvent, then add an inorganic acid aqueous solution having a concentration of 5% to 10% to the system to regulate the pH to 1 to 3, control the temperature at −10° C. to 10° C., preserve the temperature for 1 hour, perform liquid separation to obtain an organic phase, add N,N-diisopropylethylamine to the organic phase, and concentrate the system to obtain compound 5, i.e. (4S,5S)-2,2,5-trimethyl 1,3-dioxolan-4-methanoic acid having a structural formula of

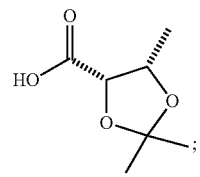

wherein the ratio of the use amount of compound 4 to that of the ether solvent is 1 g/3 to 10 ml and the molar ratio of compound 4 to N,N-diisopropylethylamine is 1:0.8 to 3;

Step 5: add compound 5 and N,N-diisopropylethylamine in the presence of an ether solvent, reduce the temperature to −30° C. to 0° C., add a chloroformate, react for 1 to 2 hours while preserving the temperature, introduce a diazomethane gas for 1 to 2 hours, add a hydrochloride ethanol solution, react for 1 to 2 hours, add an alkaline reagent to regulate the pH value to 7 to 9, perform extraction, liquid separation and concentration to obtain compound 6, i.e. (4S,5S)-2,2,5-trimethyl-5-chloroacetyl-1,3-dioxolane having a structural formula of

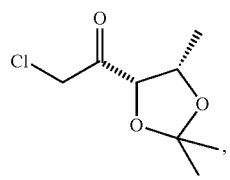

wherein the ratio of the use amount of compound 5 to that of the ether solvent is 1 g/5 to 15 ml; the molar ratio of compound 5 to N,N-diisopropylethylamine is 1:1 to 5; the molar ratio of compound 5 to the chloroformate is 1:1 to 3; and the molar ratio of compound 5 to hydrogen chloride in the hydrochloride ethanol solution is 1:1 to 5;

Step 6: add compound 6, a trinitride and a catalyst in the presence of a polar solvent, react the system at 15° C. to 40° C. for 20 to 30 hours while preserving the temperature, then perform filtering and concentration to obtain a solution of compound 7 which is used directly in the next step; compound 7 is (4S,5S)-2,2,5-trimethyl-5-(2-azidoacetyl)-1,3-dioxolane having a structural formula of

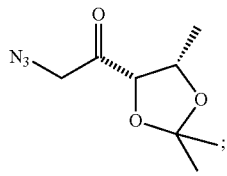

wherein the ratio of the use amount of compound 6 to that of the polar solvent is 1 g/5 to 15 ml; the molar ratio of compound 6 to the trinitride is 1:1 to 4; and the molar ratio of compound 6 to the catalyst is 1:0.05 to 0.8;

Step 7: add triphenylphosphine and water, or palladium on carbon and hydrogen, or Raney nickel and hydrogen in the presence of an ether solvent, regulate the pH of the system to 1 to 4 with an acid reagent, add a solution of compound 7, preserve the temperature at 10° C. to 30° C., react for 5 to 10 hours, perform suction filtration and concentration to obtain a filtrate containing compound 8, the filtrate being used directly in the next step or a solid of compound 8 being separated from the filtrate for use in the next step; the compound 8 is (3S, 4S)-1-amino-3,4-dihydroxy-2-pentanone having a structural formula of

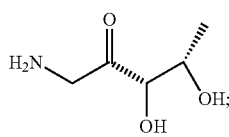

wherein the ratio of the use amount of compound 7 to that of the ether solvent is 1 g/5 to 15 ml; the molar ratio of compound 7 to triphenylphosphine is 1:0.1 to 3; the ratio of the use amount of compound 7 to that of water is 1:0.1 to 3; the mass ratio of compound 7 to palladium 5% on carbon or palladium 10% on carbon or Raney nickel is 1:0.05 to 0.6; the hydrogen is introduced until the pressure of the system is 0.4 to 0.9 MPa;

Step 8: add a catalyst, compound A, i.e. 2-amino-6-chloro-5-nitro-3H-pyrimidin-4-one having a structural formula of

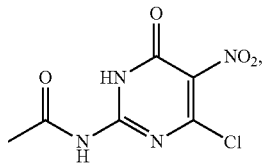

compound 8, and an alkaline reagent in the presence of an alcoholic solvent and pure water, react the system at 30° C. to 80° C. for 4 to 8 hours while preserving the temperature, add a buffer solution to regulate the pH of the system to 6 to 8, and filter the system to obtain compound 9, i.e. 2-acetylamino-5-nitro-6-((3S,4S)-3,3-dihydroxy-2-oxo-pentylamino)-pyrimidin-4-one having a structural formula of

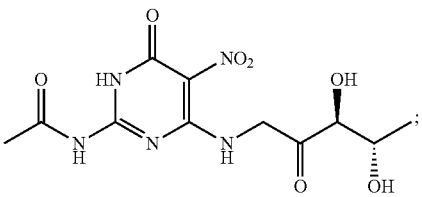 [SMILES: CC(=O)Nc1nc(NCC(=O)[C@@H](O)[C@H](C)O)c([N+](=O)[O-])c(=O)[nH]1]

wherein the ratio of the use amount of compound 8 to that of the alcoholic solvent is 1 g/5 to 15 ml; the ratio of the use amount of compound 8 to that of pure water is 1 g/1 to 5 ml; the molar ratio of compound 8 to compound A is 1:1 to 1.5; the molar ratio of compound 8 to the catalyst is 1:0.05 to 0.5; and the molar ratio of compound 8 to the alkaline reagent is 1:3 to 8;

Step 9: add a catalyst in the presence of compound 9 and a polar solvent, introduce hydrogen until the pressure of the system is 0.4 to 0.9 MPa, control the temperature of the system at 15° C. to 30° C. and the pressure at 0.4 to 0.9 MPa, react for 18 to 24 hours, filter the system, and regulate the pH of the system to 11 to 12 with an alkaline reagent to obtain a solution of compound 10 to be used directly in the next step, compound 10 is acetylamino-7,8-dihydropteridine having a structural formula of

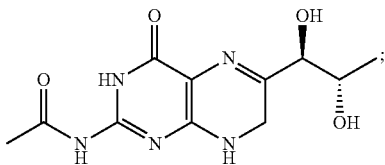 [SMILES: CC(=O)Nc1nc2c(c(=O)[nH]1)N=C([C@@H](O)[C@H](C)O)CN2]

wherein the ratio of the use amount of compound 9 to that of the polar solvent is 1 g/20 to 50 ml and the mass ratio of compound 9 to the catalyst is 1:0.05 to 0.6;

Step 10: add a catalyst in the presence of the solution of the compound 10 obtained in Step 9, introduce hydrogen until the pressure of the system is 0.4 to 0.9 MPa, control the temperature of the system at 10° C. to 30° C., control the pressure at 0.4 to 0.9 MPa, react for 72 to 84 hours, perform quenching in dilute hydrochloric acid having a concentration of 10% to 20% after reacting thoroughly, and perform suction filtration and drying to the system to obtain compound 11, i.e. a target product, a sapropterin dihydrochloride crude product, and further crystallize and purify the sapropterin dihydrochloride crude product with an alcoholic solvent or a ketone solvent at 0° C. to 40° C. to obtain a sapropterin dihydrochloride pure product, wherein the mass ratio of compound 10 to the catalyst is 1:0.05 to 0.6; the molar ratio of compound 10 to hydrochloric acid is 1:3 to 10; and the ratio of the use amount of compound 10 to that of the alcoholic solvent or the ketone solvent is 1 g/5 to 25 ml.

The oxidant in Step 1 is N-bromobutanimide, meta-chloroperoxybenzoic acid, hydrogen peroxide having a concentration of 35% or a toluene solution of tert-butyl hydroperoxide having a concentration of 50%, preferably N-bromobutanimide, meta-chloroperoxybenzoic acid or a toluene solution of tert-butyl hydroperoxide having a concentration of 50%, and optimally N-bromobutanimide;

the molar ratio of

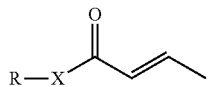

to the samarium catalyst is 1:0.05 to 0.4, preferably 1:0.05 to 0.3; the molar ratio of

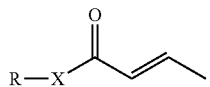

to (R)-(+)-1,1'-bi-2-naphthol is 1:0.05 to 0.4, preferably 1:0.05 to 0.3; the molar ratio of

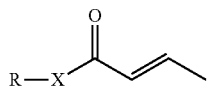

to triphenylphosphine oxide is 1:0.05 to 0.4, preferably 1:0.05 to 0.3; the mass ratio of

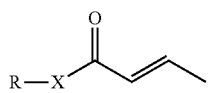

to the 4A molecular sieve is 1:6 to 12, preferably 1:7 to 10; the molar ratio of

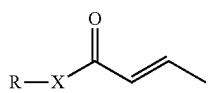

to the oxidant is 1:0.5 to 2.5, preferably 1:0.5 to 2 and the molar ratio of

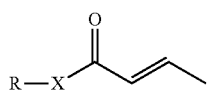

to citric acid is 1:0.05 to 0.4, preferably 1:0.05 to 0.3.

In Step 2, the Lewis acid is aluminium chloride, ferric chloride, zinc chloride, a boron trifluoride diethyl etherate solution, zinc bromide, or lithium chloride, preferably aluminium chloride, the boron trifluoride diethyl etherate solution, zinc bromide or lithium chloride, and optimally the boron trifluoride diethyl etherate solution or zinc bromide; the inorganic base is sodium bicarbonate, sodium carbonate, sodium hydroxide, potassium hydroxide, potassium carbonate or potassium bicarbonate, preferably sodium bicarbonate, sodium carbonate, potassium carbonate or potassium bicarbonate, optimally sodium carbonate;

the ratio of the use amount of compound 2 to that of acetone is 1:1 to 3.5, preferably 1:1 to 3; the ratio of the use amount of compound 2 to that of the Lewis acid is 1:0.1 to 0.8, preferably 1:0.1 to 0.6; the ratio of the use amount of compound 2 to that of the inorganic base is 1:0.5 to 2.5, preferably 1:0.5 to 2.

In Step 3, the polar solvent is tetrahydrofuran, methanol or ethanol, preferably tetrahydrofuran or methanol, optimally methanol; the resolving reagent is L-α-phenylethylamine or L-α-amphetamine, preferably L-α-phenylethylamine; the alkaline solution is a methanol solution of sodium methoxide having a concentration of 29%, a potassium hydroxide aqueous solution having a concentration of 20% or a sodium hydroxide aqueous solution having a concentration of 20%, preferably the methanol solution of sodium methoxide having a concentration of 29% or the potassium hydroxide aqueous solution having a concentration of 20%, optimally the methanol solution of sodium methoxide having a concentration of 29%;

the ratio of the use amount of compound 3 to that of the polar solvent used in the reaction is 1 g/3 to 8 ml, preferably 1 g/4 to 8 ml; the molar ratio of compound 3 to pure water is 1:0.5 to 1.8, preferably 1:0.5 to 1.5; the molar ratio of compound 3 to the alkaline substance in the alkaline solution is 1:0.5 to 1.8, preferably 1:0.5 to 1.5; the ratio of the use amount of compound 3 to that of the polar solvent for dissolving the filter cake is 1 g/3 to 8 ml, preferably 1 g/3 to 7 ml; the molar ratio of compound 3 to the resolving reagent is 1:1 to 4, preferably 1:1 to 3.

In Step 4, the ether solvent is tetrahydrofuran, 2-methyltetrahydrofuran, methyl tert-butyl ether, 1,4-dioxane or ether, preferably tetrahydrofuran, 2-methyltetrahydrofuran, methyl tert-butyl ether or 1,4-dioxane, optimally 2-methyltetrahydrofuran or 1,4-dioxane; the inorganic acid is sulphuric acid, hydrochloric acid or phosphoric acid, preferably sulfuric acid or hydrochloric acid, optimally sulfuric acid; the ratio of the use amount of compound 4 to that of the ether solvent is 1 g/3 to 8 ml, preferably 1 g/3 to 6 ml; and the molar ratio of compound 4 to N,N-diisopropylethylamine is 1:0.8 to 2.5, preferably 1:0.8 to 2.

In Step 5, the ether solvent is tetrahydrofuran, 2-methyltetrahydrofuran, methyl tert-butyl ether, 1,4-dioxane or ether, preferably tetrahydrofuran, 2-methyltetrahydrofuran or methyl tert-butyl ether, optimally tetrahydrofuran or 2-methyltetrahydrofuran; the chloroformate is methyl chloroformate, ethyl chloroformate, or propyl chloroformate, preferably methyl chloroformate or ethyl chloroformate, optimally ethyl chloroformate; the alkaline reagent is triethylamine, sodium carbonate, potassium carbonate, sodium bicarbonate, potassium bicarbonate, sodium hydroxide or potassium hydroxide, preferably triethylamine, sodium carbonate, potassium carbonate, sodium hydroxide or potassium hydroxide, optimally triethylamine; the ratio of the use amount of compound 5 to that of the ether solvent is 1 g/6 to 12 ml, preferably 1 g/8 to 12 ml; the molar ratio of compound 5 to N,N-diisopropylethylamine is 1:1.5 to 4, preferably 1:2 to 4; the molar ratio of compound 5 to the chloroformate is 1:1 to 2.5, preferably 1:1 to 2; and the molar ratio of compound 5 to hydrogen chloride in the hydrochloride ethanol solution is 1:1.5 to 4.5, preferably 1:2 to 4.

In Step 6, the polar solvent is acetonitrile, methanol, ethanol, acetone or tetrahydrofuran, preferably methanol, ethanol or acetone, optimally acetone; the catalyst is sodium iodide or potassium iodide, preferably potassium iodide; the trinitride is sodium azide or azidotrimethylsilane, preferably sodium azide; the ratio of the use amount of compound 6 to that of the polar solvent is 1 g/6 to 12 ml, preferably 1 g/8 to 12 ml; the molar ratio of compound 6 to the trinitride is 1:1 to 3, preferably 1:1 to 2.5; and the molar ratio of compound 6 to the catalyst is 1:0.05 to 0.6, preferably 0.1 to 0.5.

In Step 7, the ether solvent is tetrahydrofuran, 2-methyltetrahydrofuran, methyl tert-butyl ether, 1,4-dioxane or ether, preferably tetrahydrofuran, 2-methyltetrahydrofuran, methyl tert-butyl ether, or 1,4-dioxane, optimally tetrahydrofuran; the acid reagent is citric acid, p-toluenesulfonic acid, benzenesulfonic acid, formic acid, acetic acid, hydrochloric acid, sulfuric acid or phosphoric acid, preferably citric acid, p-toluenesulfonic acid, benzenesulfonic acid, hydrochloric acid or sulfuric acid, optimally citric acid or hydrochloric acid; the ratio of the use amount of compound 7 to that of the ether solvent is 1 g/5 to 12 ml, preferably 1 g/6 to 12 ml; the molar ratio of compound 7 to triphenylphosphine is 1:0.6 to 2, preferably 1:0.8 to 2; the ratio of the use amount of compound 7 to that of water is 1:0.6 to 2, preferably 1:0.8 to 2; the mass ratio of compound 7 to palladium 5% on carbon or palladium 10% on carbon or Raney nickel is 1:0.05 to 0.4, preferably 1:0.05 to 0.3; the hydrogen is introduced until the pressure of the system is 0.5 to 0.8 MPa, preferably 0.6 to 0.8 MPa.

In Step 8, the alcoholic solvent is methanol, ethanol, propanol or isopropanol, preferably methanol, ethanol or isopropanol, optimally isopropanol or ethanol; the catalyst is sodium iodide or potassium iodide, preferably sodium iodide; the alkaline reagent is triethylamine, diisopropylethylamine, diisopropylamine, pyridine, sodium bicarbonate, potassium bicarbonate, sodium carbonate, potassium carbonate or cesium carbonate, preferably triethylamine, pyridine, sodium bicarbonate, potassium bicarbonate, sodium carbonate or potassium carbonate, optimally triethylamine; the buffer solution is a sodium dihydrogen phosphate-disodium hydrogen phosphate aqueous solution, a potassium dihydrogen phosphate-dipotassium hydrogen phosphate aqueous solution or an ammonium formate-ammonia aqueous solution, preferably the sodium dihydrogen phosphate-disodium hydrogen phosphate aqueous solution or the potassium dihydrogen phosphate-dipotassium hydrogen phosphate aqueous solution, optimally the potassium dihydrogen phosphate-dipotassium hydrogen phosphate aqueous solution; the ratio of the use amount of compound 8 to that of the alcoholic solvent is 1 g/6 to 12 ml, preferably 1 g/6 to 10 ml; the ratio of the use amount of compound 8 to that of pure water is 1 g/1 to 4 ml, preferably 1 g/1 to 3 ml; the molar ratio of compound 8 to compound A is 1:1 to 1.4, preferably 1:1 to 1.2; the molar ratio of compound 8 to the catalyst is 1:0.1 to 0.4, preferably 1:0.1 to 0.3; and the molar ratio of compound 8 to the alkaline reagent is 1:4 to 7, preferably 1:4 to 6.

In Step 9, the catalyst is Raney nickel, 5% palladium on carbon, 10% palladium on carbon, platinum dioxide or 20% palladium on carbon, preferably Raney nickel, 5% palladium on carbon or 10% palladium on carbon, optimally Raney nickel; the polar solvent is pure water, methanol or ethanol, preferably pure water and methanol, optimally pure water; the alkaline solution is sodium hydroxide, potassium hydroxide, sodium carbonate or potassium carbonate, preferably sodium hydroxide or sodium carbonate, optimally sodium hydroxide; the ratio of the use amount of compound 9 to that of the polar solvent is 1 g/25 to 45 ml, preferably 1 g/30 to 40 ml and the mass ratio of compound 9 to the catalyst is 1:0.05 to 0.5, preferably 1:0.1 to 0.4.

In Step 10, the catalyst is Raney nickel, 5% palladium on carbon, 10% palladium on carbon, platinum dioxide or 20% palladium on carbon, preferably Raney nickel, platinum dioxide or 20% palladium on carbon, optimally 20% palladium on carbon; the alcoholic solvent is methanol, ethanol, isopropanol or n-butanol, preferably methanol, ethanol or isopropanol, optimally methanol; the ketone solvent is acetone or butanone, preferably acetone;

the mass ratio of compound 10 to the catalyst is 1:0.05 to 0.5, preferably 1:0.1 to 0.4; the molar ratio of compound 10 to hydrochloric acid is 1:4 to 9, preferably 1:5 to 8; and the ratio of the use amount of compound 10 to that of the alcoholic solvent or the ketone solvent is 1 g/5 to 20 ml, preferably 1 g/10 to 20 ml.

The present disclosure has the following advantages: 1. raw materials applied by the synthesis method are readily available, and the cost is significantly reduced compared with the prior art; 2. the route of the present disclosure is simple, thus greatly reducing a synthesis route of sapropterin dihydrochloride; 3. technological conditions are stable, the whole operation process is simple with less discharge of waste water, waste gas, and waste residues, and less pollution, hence providing an effective scheme for mass industrial production of sapropterin dihydrochloride; 4. the present disclosure introduces a chiral center in an asymmetric synthesis manner, uses a tetrahydrofuran solution containing a samarium catalyst as a catalyst and obtains a target compound having a high antimer isomerism value by means of selective catalysis; the yield is improved, and resolving operation in a racemization route is simplified; 5. the present disclosure can obtain a target product with a purity higher than 98% and an enantiomeric excess as high as more than 98%.

BRIEF DESCRIPTION OF THE DRAWINGS

The accompanying drawings of the specification are used for providing further understanding to the present disclosure and constitute a part of the present disclosure. The exemplary embodiments of the present disclosure and the illustrations thereof are used for explaining the present disclosure, instead of constituting an improper limitation to the present disclosure. In the accompanying drawings:

FIG. 1 is a flowchart of a process of a method for synthesizing sapropterin dihydrochloride involved in the present disclosure.

DETAILED DESCRIPTION

It should be noted that, if there is no conflict, the embodiments in the present disclosure and the characteristics in the embodiments can be combined with one another. The present disclosure will be described in details below with reference to the accompanying drawings and in combination with the embodiments.

The ranges in the embodiments are caused by certain fluctuation of the temperatures and pH values as reactions progress in an experiment.

Embodiment 1: main raw material: methyl crotonate

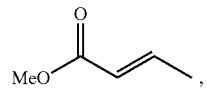

R=Me and X=O

Step 1: add 610.4 kg (0.14 eq) of a tetrahydrofuran solution containing a samarium catalyst having a concentration of 6%, 45.8 kg of (R)-(+)-1,1'-bi-2-naphthol (0.2 eq), 44.5 kg of triphenylphosphine oxide (0.2 eq), and 640 kg (8 kg/kg) of a 4 Å molecular sieve to a 3000 L reaction kettle, after stirring uniformly, control the system temperature at 15±5° C., add 213.3 kg (1.5 eq) of N-bromobutanimide, add 80 kg (1 eq) of methyl crotonate

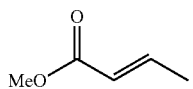

after adding N-bromobutanimide, react for 30 hours while preserving the temperature, add 53.2 kg (0.28 eq) of citric acid to the system to stop the reaction, and perform centrifugation, concentration and rectification to obtain 60.3 kg of (2S,3R)-2,3-epoxy-methyl butyrate

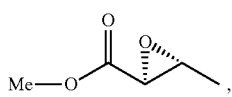

with a yield of 65%;

Step 2: add 60 kg (2 eq) of acetone, and 31.2 kg (0.2 eq) of a boron trifluoride diethyl etherate solution having a concentration of 47% to a 500 L enamel vessel, control the temperature at 20±5° C., add 60 kg (1 eq) of (2S,3R)-2,3-epoxy-methyl butyrate

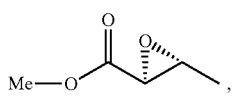

react for 7 hours while preserving the temperature, add 780 kg (1 eq) of a sodium carbonate aqueous solution having a concentration of 7%, and perform liquid separation, extraction and concentration to the system to obtain 76.6 kg of (4S,5S)-2,3-acetonide-methyl butyrate

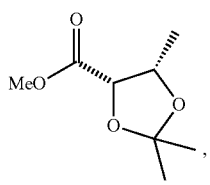

with a yield of 85%;

Step 3: add 515 L (6.7 ml/g) of tetrahydrofuran, and 76.6 kg (1 eq) of (4S,5S)-2,3-acetonide-methyl butyrate

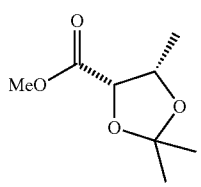

to a 1000 L reaction kettle, increase the temperature to 30±5° C., add 9.1 kg (1.1 eq) of pure water and 96 kg (1 eq) of a methanol solution of sodium methoxide having a concentration of 29%, react for 5 hours while preserving the temperature, perform centrifugation, dissolve a filter cake in 461 L (6 ml/g) of methanol, add 107 kg (2 eq) of L-α-phenylethylamine, preserve the temperature at 25±5° C. for 4 hours, and perform centrifugation and drying to obtain 80.4 kg of (4S, 5S)-2,3-acetonide-phenylethylamine butyrate

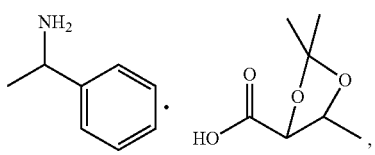

with a yield of 65%;

Step 4: add 28 L (5 ml/g) of 2-methyltetrahydrofuran, and 5.6 kg (1 eq) of 1-phenyltehanamine (4S,5S)-2,2,5-tri methyl-1,3-dioxolane-4-carboxylate

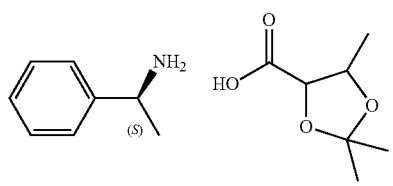

to a 72 L reaction bottle, then add a dilute hydrochloric acid aqueous solution having a concentration of 8% to the system to regulate the pH at 2±0.5, control the temperature at 0±5° C., react for 1 hour while preserving the temperature, perform liquid separation to obtain an organic phase, add 4.5 kg of (1 eq) N,N-diisopropylethylamine to the organic phase, and concentrate the system to obtain 3.0 kg of (4S,5S)-2,2,5-trimethyl-1,3-dioxolan-4-methanoic acid

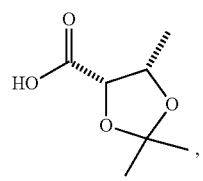

with a yield of 95%;

Step 5: add 30 L (10 ml/g) of 2-methyltetrahydrofuran, 3.0 kg of (4S,5S)-2,2,5-trimethyl-1,3-dioxolan-4-methanoic acid

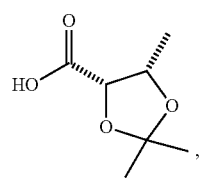

and 4.3 kg (2 eq) of N,N-diisopropylethylamine to a 72 L reaction bottle, reduce the temperature to −20±5° C., add 2.7 kg (1.3 eq) of ethyl chloroformate, react for 1.5 hours while preserving the temperature, introduce a diazomethane gas for 1.5 hours, add 10.3 kg (3 eq) of a hydrochloride ethanol solution having a concentration of 20%, react for 1.5 hours, add triethylamine to regulate the PH value to 8±0.5, and perform extraction, liquid separation and concentration to obtain 3.1 kg of (4S,5S)-2,2,5-trimethyl-5-chloroacetyl-1,3-dioxolane

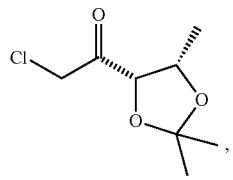

with a yield of 85%;

Step 6: add 31 L (10 ml/g) of an acetone solution, 3.1 kg of (4S,5S)-2,2,5-trimethyl-5-chloroacetyl-1,3-dioxolane

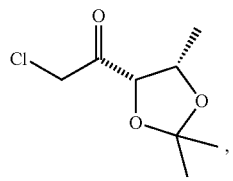

1.9 kg (1.8 eq) of sodium azide, and 0.5 kg (0.2 eq) of sodium iodide to a 72 L bottle, react the system for 25 hours while preserving the temperature at 30±5° C., perform filtering and concentration to obtain an acetone solution containing 3.05 kg of (4S,5S)-2,2,5-trimethyl-5-(2-azidoacetyl)-1,3-dioxolane

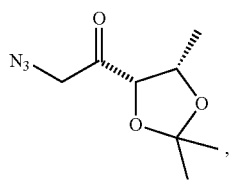

with a yield of 95%;

Step 7: add 30.5 L (10 ml/g) of tetrahydrofuran, 4.4 kg (1.1 eq) of triphenylphosphine, and 0.3 kg (1.1 eq) of water to a 100 L reaction kettle, regulate the pH of the system to 3±0.5 with citric acid, add the acetone solution containing 3.05 kg (1 eq) of (4S,5S)-2,2,5-trimethyl-5-(2-azidoacetyl)-1,3-dioxolane

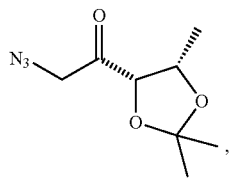

preserving the temperature at 20±5° C., react for 8 hours, perform suction filtration and concentration to obtain a filtrate containing 1.8 kg of (3S,4S)-1-amino-3,4-dihydroxy-2-pentanone

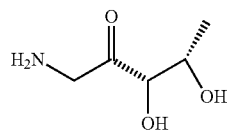

which is directly used in the next step, with a yield of 90%;

Step 8: add 18.9 L (9 ml/g) of isopropanol, 2.3 L (1.1 ml/g) of pure water, 0.1 kg of (0.1 eq) of sodium iodide, 1.76 kg (1.1 eq) of compound A (2-amino-6-chloro-5-nitro-3H-pyrimidin-4-one), 0.92 kg (1 eq) of (3S,4S)-1-amino-3,4-dihydroxy-2-pentanone

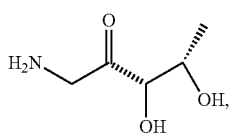

and 3.5 kg (5 eq) of triethylamine to a 50 L reaction bottle, react the system for 6 hours while preserving the temperature at 50±5° C., then add a potassium dihydrogen phosphate-dipotassium hydrogen phosphate aqueous solution to regulate the pH of the system to 7±0.5; and filter the system to obtain 1.02 kg of 2-acetylamino-5-nitro-6((3S,4S)-3,3-dihydroxy-2-oxo-pentylamino)-pyrimidin-4-one

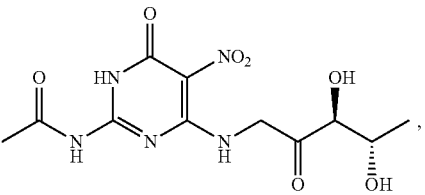 [SMILES: CC(=O)Nc1nc(NCC(=O)[C@@H](O)[C@H](C)O)c([N+](=O)[O-])c(=O)[nH]1]

with a yield of 45%; Step 9: add 2.0 kg (1 eq) of 2-acetylamino-5-nitro-6((3S,4S)-3,3-dihydroxy-2-oxo-pentylamino)-pyrimidin-4-one

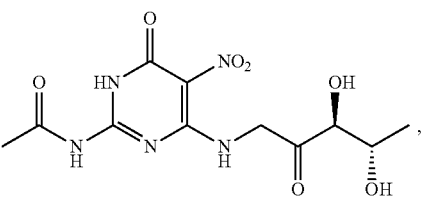 [SMILES: CC(=O)Nc1nc(NCC(=O)[C@@H](O)[C@H](C)O)c([N+](=O)[O-])c(=O)[nH]1]

70 L (35 ml/g) of pure water and 0.6 kg (0.3 g/g) of Raney nickel to a 100 L autoclave, introduce hydrogen until the pressure of the reaction system is 0.6±0.05 MPa, control the temperature of the system at 20±5° C. and the pressure at 0.6±0.05 MPa, react for 20 hours, filter the system, and regulate the pH to 11.5±0.5 to obtain of an aqueous solution containing 1.7 kg of acetylamino-7,8-dihydropteridine

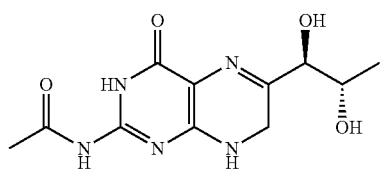 [SMILES: CC(=O)Nc1nc2c(c(=O)[nH]1)N=C([C@@H](O)[C@H](C)O)CN2]

which is used directly in the next step;

Step 10: add 0.255 kg (0.15 g/g) of palladium 20% on carbon to the aqueous solution containing 1.7 kg of acetylamino-7,8-dihydropteridine

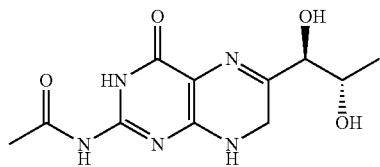 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.6±0.05 MPa, control the temperature of the system at 20±5° C. and the pressure at 0.6±0.05 MPa, react for 80 hours, after reacting thoroughly, perform quenching in 10.29 kg (7 eq) of dilute hydrochloric acid having a concentration of 15%, and perform suction filtration and drying to the system to obtain a target product, i.e. a sapropterin dihydrochloride

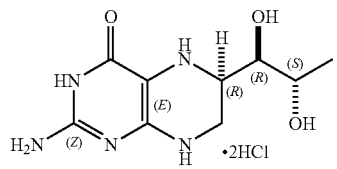

crude product, recrystallize and purify the crude product by 25 L (14.7 ml/g) of methanol at 20±5° C. to obtain 0.95 kg of a pure product, with a yield of 50%, a purity of 98.5% and an enantiomeric excess of 99.2%.

Embodiment 2: main raw material:

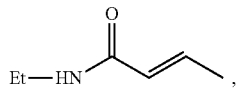

R=Et and X=NH

Step 1: add 1638 kg (1 eq) of a tetrahydrofuran solution containing a samarium catalyst having a concentration of 10%, 143.2 kg of (R)-(+)-1,1'-bi-2-naphthol (0.5 eq), 139 kg of triphenylphosphine oxide (0.5 eq), and 1698 kg (15 kg/kg) of a 4 A molecular sieve to a 3000 L reaction kettle, after stirring uniformly, control the system temperature at 25±5° C., add 518 kg (3 eq) of meta-chloroperoxybenzoic acid, subsequently, add 113.2 kg (1 eq) of acetylamido crotonate

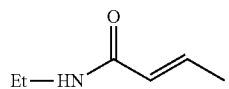

after adding meta-chloroperoxybenzoic acid, react for 36 hours while preserving the temperature, add 96 kg (0.5 eq) of citric acid to the system to stop the reaction, and perform centrifugation, concentration and rectification to the system to obtain 78.8 kg of (2S,3R)-2,3-epoxy-acetylamido butyrate

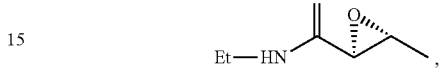

with a yield of 61%;

Step 2: add 141.7 kg (4 eq) of acetone, and 98.8 kg (1 eq) of ferric chloride to a 1000 L enamel vessel, control the temperature at 30±5° C., add 78.8 kg (1 eq) of (2S,3R)-2,3-epoxy-acetylamido butyrate

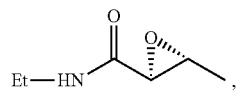

react for 10 hours while preserving the temperature, add 732 kg (3 eq) of a sodium hydroxide aqueous solution having a concentration of 10%, and perform liquid separation, extraction and concentration to the system to obtain 93.1 kg of (4S,5S)-2,3-acetonide-ethylbutyramide

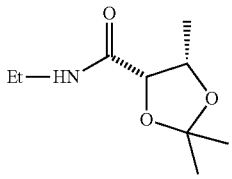

with a yield of 81.5%;

Step 3: add 931 L (10 ml/g) of methanol, and 93.1 kg (1 eq) of (4S,5S)-2,3-acetonide-ethylbutyramide

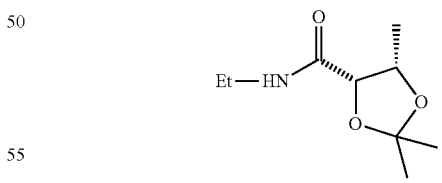

to a 2000 L reaction kettle, increase the temperature to 40±5° C., add 26.9 kg (3 eq) of pure water and 199 kg (2 eq) of a sodium hydroxide aqueous solution having a concentration of 20%, react for 8 hours while preserving the temperature, perform centrifugation, dissolve a filter cake in 931 L (10 ml/g) of tetrahydrofuran, add 300 kg (5 eq) of L-α-phenylethylamine, preserve the temperature at 35±5° C. for 5 hours, and perform centrifugation and drying to obtain 85.3 kg of (4S,5S)-2,2,5-trimethyl-1,3-di oxolan-4-phenylacetylamino carboxylate

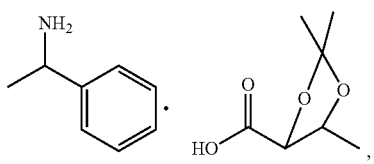

with a yield of 61%;

Step 4: add 26 L (10 ml/g) of tetrahydrofuran, 2.6 kg (1 eq) of (4S,5S)-2,2,5-trimethyl-1,3-dioxolan-4-phenylacetylamino carboxylate

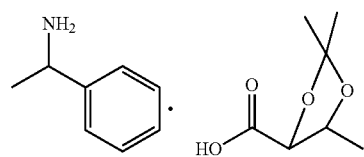

to a 72 L reaction bottle, then add a dilute hydrochloric acid aqueous solution having a concentration of 10% to the system to regulate the pH at 3±0.5, control the temperature at 10±5° C., react for 1 hour, perform liquid separation to obtain an organic phase, add 6.1 kg of (3 eq) N,N-diisopropylethylamine to the organic phase, and concentrate the system to obtain 1.3 kg of (4S,5S)-2,2,5-trimethyl-1,3-dioxolan-4-methanoic acid

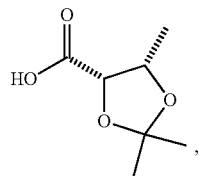

with a yield of 90%;

Step 5: add 20 L (15 ml/g) of tetrahydrofuran, 1.3 kg of (4S,5S)-2,2,5-trimethyl-1,3-dioxolan-4-methanoic acid

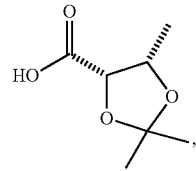

and 8 kg (5 eq) of N,N-diisopropylethylamine to a 72 L reaction bottle, reduce the temperature to 0±5° C., add 2.9 kg (3 eq) of propyl chloroformate, react for 1 to 2 hours while preserving the temperature, introduce a diazomethane gas for 2 hours, add 12.7 kg (5 eq) of a hydrochloride ethanol solution having a concentration of 20%, react for 2 hours, add sodium carbonate to regulate the PH value to 9±0.5, and perform extraction, liquid separation and concentration to obtain 1.3 kg of (4S,5S)-2,2,5-trimethyl-5-chloroacetyl-1,3-dioxolane

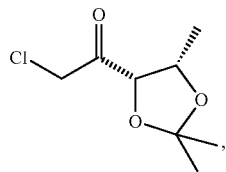

with a yield of 82%;

Step 6: add 19.5 L (15 ml/g) of an acetonitrile solvent, 1.3 kg of (4S,5S)-2,2,5-trimethyl-5-chloroacetyl-1,3-dioxolane

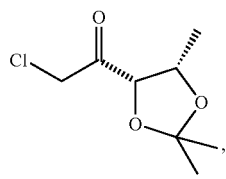

3.1 kg (4 eq) of azidotrimethylsilane, and 0.8 kg (0.8 eq) of sodium iodide to a 72 L bottle, react the system for 30 hours while preserving the temperature at 40±5° C., perform filtering and concentration to obtain an acetonitrile solution containing 1.21 kg of

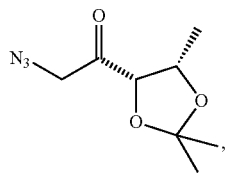

with a yield of 90%;

Step 7: add 18.2 L (15 ml/g) of 1,4-dioxane and 0.73 kg (0.6 g/g) of Raney nickel to a 50 L reaction kettle, introduce hydrogen until the system pressure is 0.9±0.1 MPa, regulate the pH of the system to 1±0.5 with concentrated hydrochloric acid, add the acetonitrile solution containing 1.21 kg (1 eq) of (4S,5S)-2,2,5-trimethyl-5-(2-azidoacetyl)-1,3-dioxolane

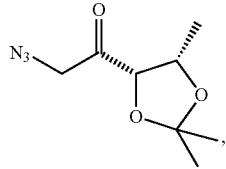

preserve the temperature at 30±5° C., react for 8 hours, perform suction filtration and concentration to obtain 0.71 kg of (3S,4S)-1-amino-3,4-dihydroxy-2-pentanone

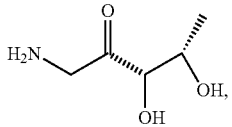

with a yield of 87.5%;

Step 8: add 47.5 L (15 ml/g) of methanol, 15.8 L (5 ml/g) of pure water, 1.28 kg of (0.5 eq) of potassium iodide, 3.6 kg (1.5 eq) of compound A (2-amino-6-chloro-5-nitro-3H-pyrimidin-4-one), 1.4 kg (1 eq) of (3S,4S)-1-amino-3,4-dihydroxy-2-pentanone

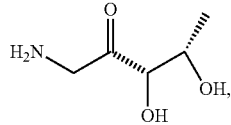

and 6.4 kg (8 eq) of pyridine to a 100 L reaction bottle, react the system for 8 hours while preserving the temperature at 80±5° C., then add an ammonium formate-ammonia aqueous solution to regulate the pH of the system to 8±0.5; and filter the system to obtain 1.47 kg of 2-acetylamino-5-nitro-6-((3S,4S)-3,3-dihydroxy-2-oxo-pentylamino)-pyrimidin-4-one

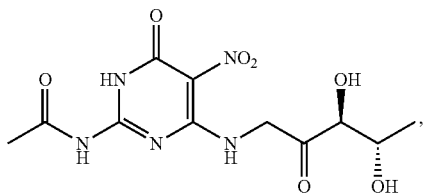 [SMILES: CC(=O)Nc1nc(NCC(=O)[C@@H](O)[C@H](C)O)c([N+](=O)[O-])c(=O)[nH]1]

with a yield of 43.2%;

Step 9: add 2.94 kg (1 eq) of 2-acetylamino-5-nitro-6-((3S,4S)-3,3-dihydroxy-2-oxo-pentylamino)-pyrimidin-4-one

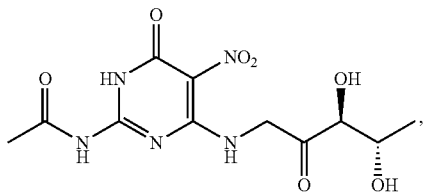 [SMILES: CC(=O)Nc1nc(NCC(=O)[C@@H](O)[C@H](C)O)c([N+](=O)[O-])c(=O)[nH]1]

147 L (50 ml/g) of methanol and 1.76 kg (0.6 g/g) of 5% palladium on carbon to a 200 L autoclave, introduce hydrogen until the pressure of the system is 0.9±0.05 MPa, control the temperature of the system at 30±5° C. and the pressure at 0.9±0.05 MPa, react for 24 hours, filter the system, and regulate the pH to 12±0.5 to obtain a methanol solution containing 2.5 kg of acetylamino-7,8-dihydropteridine

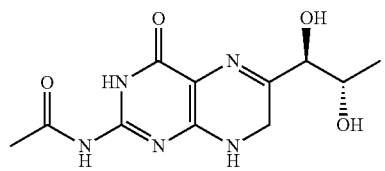 [SMILES: CC(=O)Nc1nc2c(c(=O)[nH]1)N=C([C@@H](O)[C@H](C)O)CN2]

which is used directly in the next step;

Step 10: add 1.5 kg (0.6 g/g) of Raney nickel to the methanol solution containing 2.5 kg of acetylamino-7,8-dihydropteridine

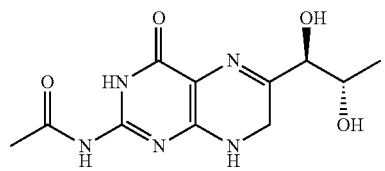 [SMILES: CC(=O)Nc1nc2c(c(=O)[nH]1)N=C([C@@H](O)[C@H](C)O)CN2]

obtained in Step 9, introduce hydrogen until the pressure of the system is 0.9±0.05 MPa, control the temperature of the system at 30±5° C. and the pressure at 0.9±0.05 MPa, react for 84 hours, after reacting thoroughly, perform quenching in 16.2 kg (10 eq) of dilute hydrochloric acid having a concentration of 20%, and perform suction filtration and drying to the system to obtain a target product, i.e. a crude product of sapropterin dihydrochloride

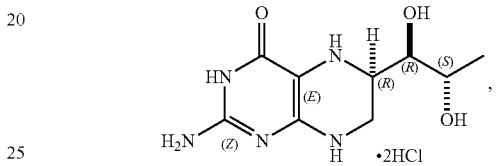

recrystallize and purify the crude product by 62.5 L (25 ml/g) of acetone at 40±5° C. to obtain 1.31 kg of a pure product, with a yield of 47%, a purity of 98.1% and an enantiomeric excess of 98.9%.

Embodiment 3: main raw material:

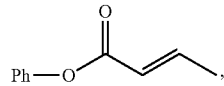

R=Pt and X=O

Step 1: add 327.6 kg (0.05 eq) of a tetrahydrofuran solution containing a samarium catalyst having a concentration of 5%, 14.3 kg (0.05 eq) of (R)-(+)-1,1'-bi-2-naphthol, 13.9 kg (0.05 eq) of triphenylphosphine oxide, and 811 kg (5 kg/kg) of a 4 A molecular sieve to a 2000 L reaction kettle, after stirring uniformly, control the system temperature at 0±5° C., add 20 kg (0.5 eq) of hydrogen peroxide having a concentration of 35%, add 162.2 kg (1 eq) of phenyl crotonate

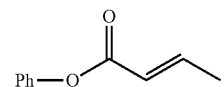

to the system after adding hydrogen peroxide, react for 20 hours while preserving the temperature, add 9.6 kg (0.05 eq) of citric acid to the system to stop the reaction, and perform centrifugation, concentration and rectification to the system to obtain 94.4 kg of (2S,3R)-2,3-epoxy-phenyl butyrate

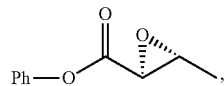

with a yield of 53%;

Step 2: add 22 kg (1 eq) of acetone, and 11.8 kg (0.1 eq) of zinc bromide to a 500 L enamel vessel, control the temperature at 10±5° C., add 94.4 kg (1 eq) of (2S,3R)-2,3-epoxyphenyl butyrate

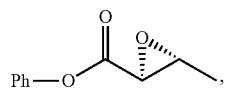

react for 5 hours while preserving the temperature, add 296 kg (0.5 eq) of a potassium hydroxide aqueous solution having a concentration of 5%, and perform liquid separation, extraction and concentration to the system to obtain 96 kg of (4S,5S)-2,2,5-trimethyl-acetonide-phenyl butyrate

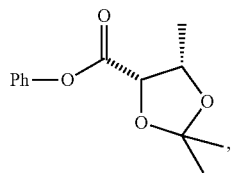 [SMILES: C[C@@H]1OC(C)(C)O[C@@H]1C(=O)Oc1ccccc1]

with a yield of 77%;

Step 3: add 288 L (3 ml/g) of ethanol, and 96 kg (1 eq) of (4S,5S)-2,2,5-trimethyl-2,3-acetonide-phenyl butyrate

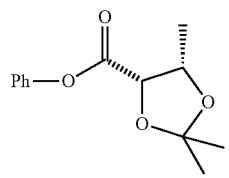 [SMILES: C[C@@H]1OC(C)(C)O[C@@H]1C(=O)Oc1ccccc1]

to a 2000 L reaction kettle, increase the temperature to 25±5° C., add 7.3 kg (0.5 eq) of pure water and 57 kg (0.5 eq) of a potassium hydroxide aqueous solution having a concentration of 20%, react for 3 hours while preserving the temperature, perform centrifugation, dissolve a filter cake in 192 L (2 ml/g) of ethanol, add 61 kg (1 eq) of L-α-amphetamine, preserve the temperature at 15±5° C. for 3 hours, and perform centrifugation and drying to obtain 69.3 kg of (4S,5S)-2,2,5-trimethyl-1,3-dioxolan-4-phenylacetylamino carboxylate

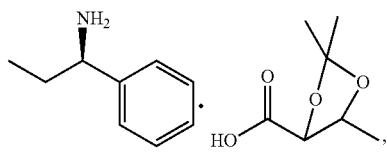

with a yield of 57.5%;

Step 4: add 30 L (3 ml/g) of 1,4-dioxane, 10 kg (1 eq) of (4S,5S)-2,2,5-trimethyl-1,3-di oxolan-4-phenylacetylamino carboxylate

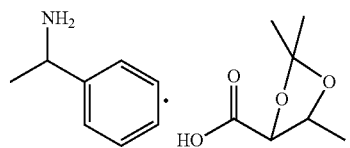

to a 72 L reaction bottle, then add a dilute phosphoric acid aqueous solution having a concentration of 5% to the system to regulate the pH at 1±0.5, control the temperature at −10±5° C., react for 1 hour, perform liquid separation to obtain an organic phase, add 3.3 kg of (0.8 eq) N,N-diisopropylethylamine to the organic phase, and concentrate the system to obtain 5.2 kg of (4S,5S)-2,2,5-trimethyl-1,3-dioxolan-4-methanoic acid

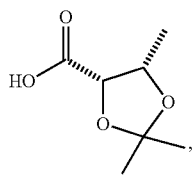

with a yield of 91%;

Step 5: add 26 L (5 ml/g) of 1,4-dioxane, 5.2 kg (1 eq) of (4S,5S)-2,2,5-trimethyl-1,3-dioxolan-4-methanoic acid

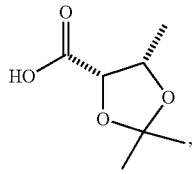

and 3.7 kg (1 eq) of N,N-diisopropylethylamine to a 72 L reaction bottle, reduce the temperature to −30±5° C., add 3.1 kg (1 eq) of methyl chloroformate, react for 1 hour while preserving the temperature, introduce a diazomethane gas for 1 hour, add 2 kg (1 eq) of a hydrochloride ethanol solution having a concentration of 20%, react for 1 hour, add potassium bicarbonate to regulate the PH value to 7±0.5, and perform extraction, liquid separation and concentration to obtain 5 kg of (4S,5S)-2,2,5-trimethyl-5-chloroacetyl-1,3-dioxolane

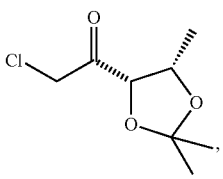

with a yield of 81%;

Step 6: add 25 L (5 ml/g) of methanol, 5 kg of (4S,5S)-2,2,5-trimethyl-5-chloroacetyl-1,3-dioxolane

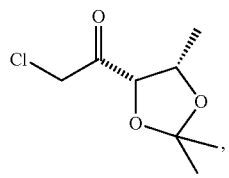

1.7 kg (1 eq) of sodium azide, and 0.22 kg (0.05 eq) of potassium iodide to a 72 L bottle, after react the system for 20 hours while preserving the temperature at 15±5° C., perform filtering and concentration to obtain a methanol solution containing 4.5 kg of (4S,5S)-2,2,5-trimethyl-5-(2-azidoacetyl)-1,3-dioxolane

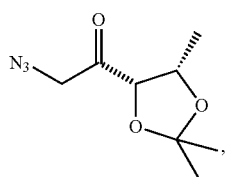

with a yield of 87%;

Step 7: add 22.5 L (5 ml/g) of methyl tert-butyl ether and 0.3 kg (0.05 g/g) of 10% palladium on carbon to a 100 L reaction kettle, introduce hydrogen until the system pressure is 0.4±0.1 MPa, regulate the pH of the system to 4±0.5 with benzenesulfonic acid, add the methanol solution containing 4.5 kg (1 eq) of (4S,5S)-2,2,5-trimethyl-5-(2-azidoacetyl)-1,3-dioxolane

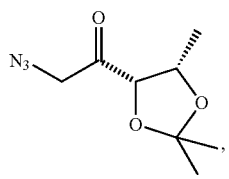

preserving the temperature at 10±5° C., react for 5 hours, perform suction filtration and concentration to obtain a filtrate containing 2.6 kg of (3S,4S)-1-amino-3,4-dihydroxy-2-pentanone

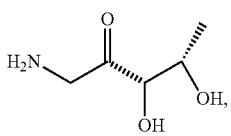

with a yield of 86%;

Step 8: add 21 L (5 ml/g) of ethanol, 4.2 L (1 ml/g) of pure water, 0.1 kg of (0.05 eq) of sodium iodide, 3.2 kg (1 eq) of compound A (2-amino-6-chloro-5-nitro-3H-pyrimidin-4-one), 1.83 kg (1 eq) of (3S,4S)-1-amino-3,4-dihydroxy-2-pentanone

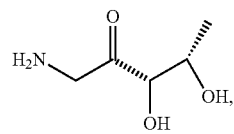

and 4.4 kg (3 eq) of sodium carbonate to a 50 L reaction bottle, react the system for 4 hours while preserving the temperature at 30±5° C., then add a sodium dihydrogen phosphate-disodium hydrogen phosphate aqueous solution to regulate the pH of the system to 6±0.5; and filter the system to obtain 1.9 kg of 2-acetylamino-5-nitro-6-((3S,4S)-3,3-dihydroxy-2-oxo-pentylamino)-pyrimidin-4-one

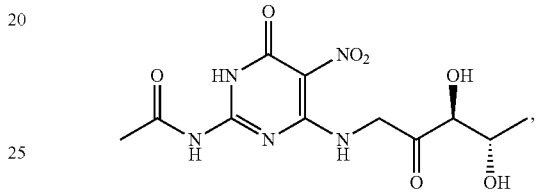

with a yield of 42%;

Step 9: add 3.8 kg (1 eq) of 2-acetylamino-5-nitro-6((3S,4S)-3,3-dihydroxy-2-oxo-pentylamino)-pyrimidin-4-one

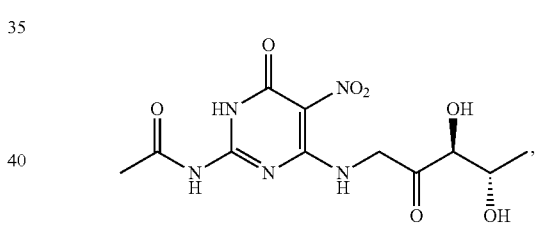

76 L (20 ml/g) of ethanol and 0.2 kg (0.05 g/g) of 20% palladium on carbon to a 100 L autoclave, introduce hydrogen until the system pressure is 0.4±0.05 MPa, control the temperature of the system at 15±5° C. and the pressure at 0.4±0.05 MPa, react for 18 hours, filter the system, and regulate the pH to 11±0.5 to obtain of an ethanol solution containing 3.25 kg of acetylamino-7,8-dihydropteridine

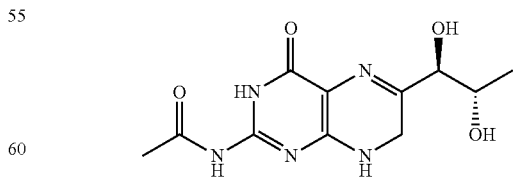

which is used directly in the next step;

Step 10: add 0.16 kg (0.05 g/g) of platinum dioxide in the presence of the ethanol solution containing 3.25 kg of acetylamino-7,8-dihydropteridine

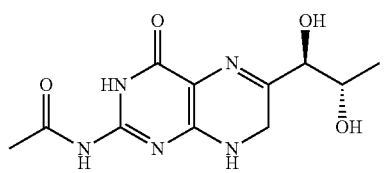 [SMILES: CC(=O)Nc1nc2c(c(=O)[nH]1)N=C([C@@H](O)[C@H](C)O)CN2]

obtained in Step 9, introduce hydrogen until the system pressure is 0.4±0.05 MPa, control the temperature of the system at 10±5° C. and the pressure at 0.4±0.05 MPa, react for 72 hours, after reacting thoroughly, perform quenching in 12.6 kg (3 eq) of dilute hydrochloric acid having a concentration of 10%, and perform suction filtration and drying to the system to obtain a target product, i.e. a crude product of sapropterin dihydrochloride

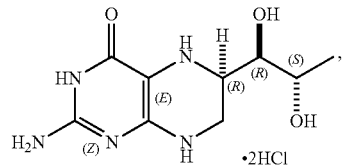

recrystallize and purify the crude product by 16.3 L (5 ml/g) of isopropanol at 0±5° C. to obtain 1.52 kg of a pure product, with a yield of 42%, a purity of 98.0% and an enantiomeric excess of 98.7%.

Embodiment 4: main raw material:

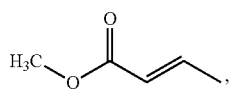

R=—CH$_3$ and X=O

Step 1: add 1214 kg (0.4 eq) of a tetrahydrofuran solution containing a samarium catalyst having a concentration of 6%, 63.7 kg (0.4 eq) of (R)-(+)-1,1'-bi-2-naphthol, 61.9 kg (0.4 eq) of triphenylphosphine oxide, and 667 kg (12 kg/kg) of a 4 A molecular sieve to a 3000 L reaction kettle, after stirring uniformly, control the system temperature at 10±5° C., add 247 kg (2.5 eq) of N-bromobutanimide, add 55.7 kg (1 eq) of methyl crotonate

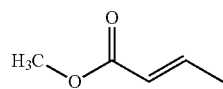

to the system after adding N-bromobutanimide, react for 30 hours while preserving the temperature, add 42.7 kg (0.4 eq) of citric acid to the system to stop the reaction, and perform centrifugation, concentration and rectification to the system to obtain 40 kg of (2S,3R)-2,3-epoxy-methyl butyrate

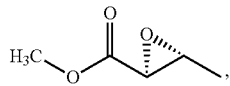

with a yield of 62%;

Step 2: add 70.1 kg (3.5 eq) of acetone, and 47 kg (0.8 eq) of zinc chloride to a 500 L enamel vessel, control the temperature at 25±5° C., add 40 kg (1 eq) of (2S,3R)-2,3-epoxymethyl butyrate

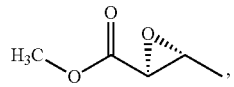

react for 8 hours while preserving the temperature, add 1190 kg (2.5 eq) of a potassium carbonate aqueous solution having a concentration of 10%, and perform liquid separation, extraction and concentration to the system to obtain 49.8 kg of (4S,5S)-2,2,5-trimethyl-acetonide-methyl butyrate

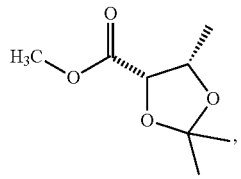

with a yield of 83%; Step 3: add 398 L (8 ml/g) of methanol, and 49.8 kg (1 eq) of (4S,5S)-2,2,5-trimethyl-acetonide-methyl butyrate

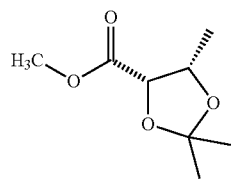

to a 1000 L reaction kettle, increase the temperature to 35±5° C., add 9.3 kg (1.8 eq) of pure water and 144.5 kg (1.8 eq) of a potassium hydroxide aqueous solution having a concentration of 20%, react for 6.5 hours while preserving the temperature, perform centrifugation, dissolve a filter cake in 398 L (8 ml/g) of methanol, add 154.7 kg (4 eq) of L-α-amphetamine, preserve the temperature at 25±5° C. for 4.5 hours, and perform centrifugation and drying to obtain 53.2 kg of (4S,5S)-2,2,5-trimethyl-2,3-acetonide-phenylacetylamino butyrate

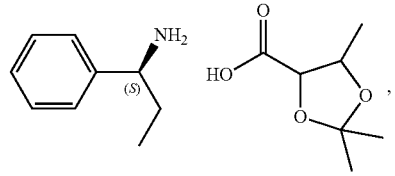

with a yield of 63%;

Step 4: add 48 L (8 ml/g) of methyl tert-butyl ether, 6 kg (1 eq) of (4S,5S)-2,2,5-trimethyl-2,3-acetonide-phenylacetylamino butyrate

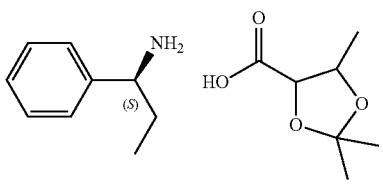 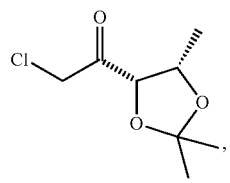

to a 72 L reaction bottle, then add a dilute hydrochloric acid aqueous solution having a concentration of 9% to the system to regulate the pH at 2.5±0.5, control the temperature at −5±5° C., react for 1 hour, perform liquid separation to obtain an organic phase, add 6.6 kg of (2.5 eq) N,N-diisopropylethylamine to the organic phase, and concentrate the system to obtain 3.0 kg of 1,3-dioxolan-4-methanoic acid 3 kg (3 eq) of sodium azide, and 1.5 kg (0.6 eq) of sodium iodide to a 72 L bottle, react the system for 27 hours while preserving the temperature at 32±5° C., perform filtering and concentration to obtain an acetone solution containing 2.8 kg of (4S,5S)-2,2,5-trimethyl-5-(2-azidoacetyl)-1,3-dioxolane

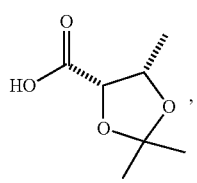 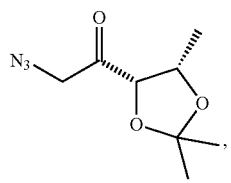

with a yield of 92%;

Step 5: add 36 L (12 ml/g) of tetrahydrofuran, 3.0 kg of (4S,5S)-2,2,5-trimethyl-1,3-dioxolan-4-methanoic acid with a yield of 91%;

Step 7: add 33.7 L (12 ml/g) of 2-methyltetrahydrofuran, 8.6 kg (2.0 eq) of triphenylphosphine, and 0.5 kg (2.0 eq) of water to a 72 L reaction kettle, regulate the pH of the system to 3±0.5 with acetic acid, add the acetone solution containing 2.8 kg of (4S,5S)-2,2,5-trimethyl-5-(2-azidoacetyl)-1,3-dioxolane

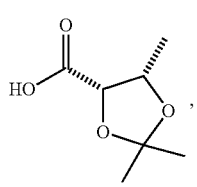 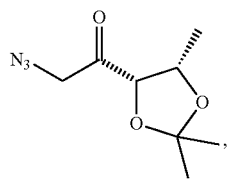

and 9.7 kg (4 eq) of N,N-diisopropylethylamine to a 72 L reaction bottle, reduce the temperature to −25±5° C., add 4.4 kg (2.5 eq) of methyl chloroformate, react for 1.5 hours while preserving the temperature, introduce a diazomethane gas for 1.5 hours, add 15.3 kg (4.5 eq) of a hydrochloride ethanol solution having a concentration of 20%, react for 1.5 hours, add triethylamine to regulate the pH value to 8.5±0.5, and perform extraction, liquid separation and concentration to obtain 3.0 kg of (4S,5S)-2,2,5-trimethyl-5-chloroacetyl-1,3-dioxolane preserving the temperature at 25±5° C., react for 8.5 hours, perform suction filtration and concentration to obtain a filtrate containing 1.6 kg of (3S,4S)-1-amino-3,4-dihydroxy-2-pentanone

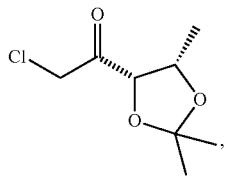 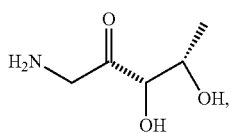

with a yield of 83%;

Step 6: add 36 L (12 ml/g) of acetone, 3 kg of (4S,5S)-2,2,5-trimethyl-5-chloroacetyl-1,3-dioxolane with a yield of 87.5%;

Step 8: add 19.7 L (12 ml/g) of methanol, 6.4 L (4 ml/g) of pure water, 0.8 kg of (0.4 eq) of sodium iodide, 4.0 kg (1.4 eq) of compound A (2-amino-6-chloro-5-nitro-3H-pyrimidin-4-one), 1.6 kg (1 eq) of (3S,4S)-1-amino-3,4-dihydroxy-2-pentanone

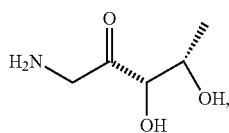

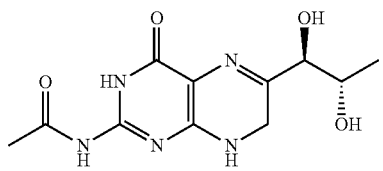

and 8.7 kg (7 eq) of potassium bicarbonate to a 50 L reaction bottle, react the system for 7 hours while preserving the temperature at 70±5° C., then add a sodium dihydrogen phosphate-disodium hydrogen phosphate aqueous solution to regulate the pH of the system to 7.5±0.5; and filter the system to obtain 1.7 kg of 2-acetylamino-5-nitro-6((3S,4S)-3,3-dihydroxy-2-oxo-pentylamino)-pyrimidin-4-one obtained in Step 9, introduce hydrogen until the pressure of the reaction kettle is 0.8±0.05 MPa, control the temperature of the system at 25±5° C. and the pressure at 0.8±0.05 MPa, react for 82 hours, after reacting thoroughly, perform quenching in 31.9 kg (9 eq) of dilute hydrochloric acid having a concentration of 15%, and perform suction filtration and drying to the system to obtain a target product, i.e. a crude product of sapropterin dihydrochloride

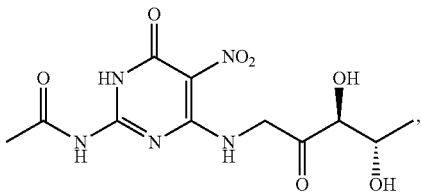 [SMILES: CC(=O)Nc1nc(NCC(=O)[C@@H](O)[C@H](C)O)c([N+](=O)[O-])c(=O)[nH]1]

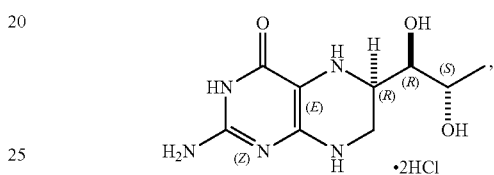

with a yield of 43%;

Step 9: add 1.7 kg (1 eq) of 2-acetylamino-5-nitro-6((3S, 4S)-3,3-dihydroxy-2-oxo-pentylamino)-pyrimidin-4-one recrystallize and purify the crude product by 29 L (20 ml/g) of methanol at 35±5° C. to obtain 0.8 kg of a pure product, with a yield of 45%, a purity of 98.3% and an enantiomeric excess of 99.1%.

Embodiment 5: main raw material:

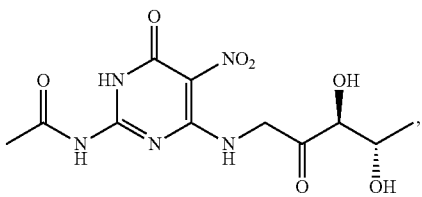 [SMILES: CC(=O)Nc1nc(NCC(=O)[C@@H](O)[C@H](C)O)c([N+](=O)[O-])c(=O)[nH]1]

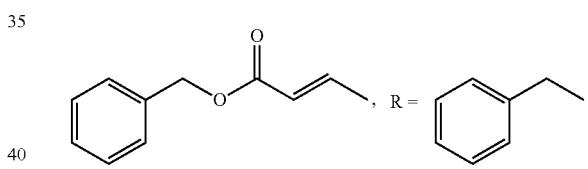

and X=O

Step 1: add 836 kg (0.3 eq) of a tetrahydrofuran solution contaning a samarium catalyst having a concentration of 4%, 29.2 kg (0.3 eq) of (R)-(+)-1,1'-bi-2-naphthol, 28.4 kg (0.3 eq) of triphenylphosphine oxide, and 600 kg (10 kg/kg) of a 4 A molecular sieve to a 3000 L reaction kettle, after stirring uniformly, control the system temperature at 20±5° C., add 117.4 kg (2 eq) of meta-chloroperoxybenzoic acid, add 60 kg (1 eq) of benzyl crotonate 78.7 L (45 ml/g) of methanol and 0.9 kg (0.5 g/g) of 5% palladium on carbon to a 100 L autoclave, introduce hydrogen until the reaction system pressure is 0.8±0.05 MPa, control the temperature of the system at 25±5° C. and the pressure at 0.8±0.05 MPa, react for 22 hours, filter the system, and regulate the pH to 11±0.5 to obtain a methanol solution containing 1.5 kg of acetylamino-7,8-dihydropteridine which is used directly in the next step;

Step 10: add 0.7 kg (0.05 g/g) of palladium 5% on carbon in the presence of the methanol solution containing 1.5 kg of acetylamino-7,8-dihydropteridine to the system after adding meta-chloroperoxybenzoic acid, react for 32 hours while preserving the temperature, add 19.6 kg (0.3 eq) of citric acid to the system to stop the reaction, and perform centrifugation, concentration and rectification to the system to obtain 40.5 kg of (2S,3R)-2,3-epoxy-benzyl butyrate

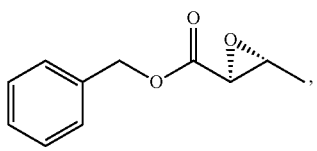

with a yield of 62%;

Step 2: add 36.8 kg (3 eq) of acetone, and 5.4 kg (0.6 eq) of lithium chloride to a 500 L enamel vessel, control the temperature at 15±5° C., add 40.5 kg (1 eq) of (2S,3R)-2,3-epoxy-benzyl butyrate

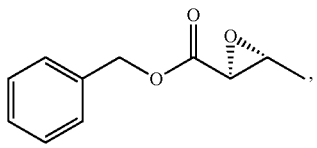

react for 7 hours while preserving the temperature, add 422 kg (2 eq) of a potassium bicarbonate aqueous solution having a concentration of 10%, and perform liquid separation, extraction and concentration to the system to obtain 44 kg of (4S,5S)-2,2,5-trimethyl-acetonide-benzyl butyrate

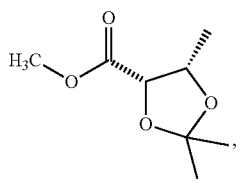

with a yield of 82%;

Step 3: add 352 L (8 ml/g) of ethanol, and 44 kg (1 eq) of (4S,5S)-2,2,5-trimethyl-2,3-acetonide-benzyl butyrate

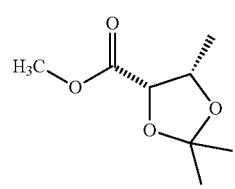

to a 1000 L reaction kettle, increase the temperature to 37±5° C., add 4.8 kg (1.5 eq) of pure water and 53.2 kg (1.5 eq) of a sodium hydroxide aqueous solution having a concentration of 20%, react for 6 hours while preserving the temperature, perform centrifugation, dissolve a filter cake in 352 L (8 ml/g) of ethanol, add 71.0 kg (3 eq) of L-α-amphetamine, preserve the temperature at 22±5° C. for 4 hours, and perform centrifugation and drying to obtain 32.4 kg of (4S,5S)-2,2,5-trimethyl-2,3-acetonide-phenylacetylamino butyrate

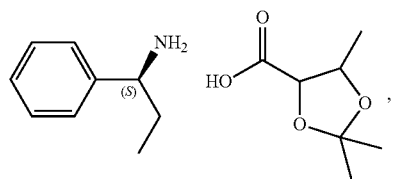

with a yield of 62%;

Step 4: add 48 L (6 ml/g) of 1,4-dioxane, 8 kg (1 eq) of (4S,5S)-2,2,5-trimethyl-2,3-acetonide-phenylacetylamino butyrate

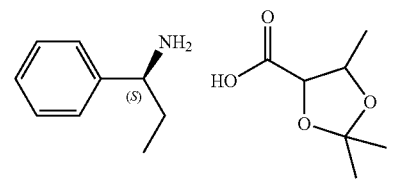

to a 72 L reaction bottle, then add a dilute sulphuric acid aqueous solution having a concentration of 10% to the system to regulate the pH at 2.5±0.5, control the temperature at −5±5° C., react for 1 hour, perform liquid separation to obtain an organic phase, add 7.0 kg of (2.0 eq) N,N-diisopropylethylamine to the organic phase, and concentrate the system to obtain 4.1 kg of (4S,5S)-2,2,5-trimethyl-1,3-dioxolan-4-methanoic acid

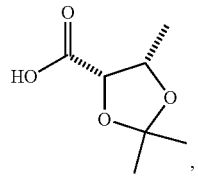

with a yield of 93.5%;

Step 5: add 49 L (12 ml/g) of 2-methyltetrahydrofuran, 4.1 kg of 1,3-dioxolan-4-methanoic acid

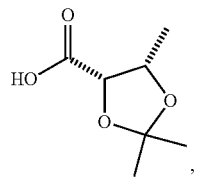

and 13.1 kg (4 eq) of N,N-diisopropylethylamine to a 100 L reaction bottle, reduce the temperature to −22±5° C., add 5.5 kg (2.0 eq) of ethyl chloroformate, react for 1.8 hours while preserving the temperature, introduce a diazomethane gas for 1.8 hours, add 18.5 kg (4.5 eq) of a hydrochloride ethanol solution having a concentration of 20%, react for 1.8 hours, add potassium bicarbonate to regulate the pH value to 8.5±0.5, and perform extraction, liquid separation and concentration to obtain 4.1 kg of (4S,5S)-2,2,5-trimethyl-5-chloroacetyl-1,3-dioxolane

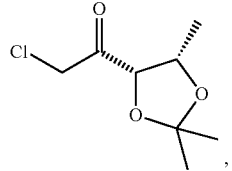

with a yield of 83.7%;

Step 6: add 49 L (12 ml/g) of acetone, 4.1 kg of (4S,5S)-2,2,5-trimethyl-5-chloroacetyl-1,3-dioxolane

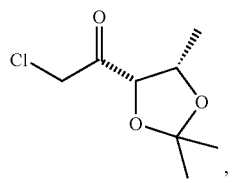

3.4 kg (2.5 eq) of sodium azide, and 1.8 kg (0.5 eq) of potassium iodide to a 72 L bottle, react the system for 26 hours while preserving the temperature at 34±5° C., perform filtering and concentration to obtain an acetone solution containing 3.9 kg of (4S,5S)-2,2,5-trimethyl-5-(2-azidoacetyl)-1,3-dioxolane

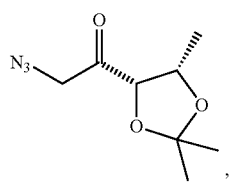

with a yield of 91.5%;

Step 7: add 46.4 L (12 ml/g) of methyl tert-butyl ether and 1.2 kg (0.3 g/g) of Raney nickel to a 100 L reaction kettle, introduce hydrogen until the system pressure is 0.8±0.1 MPa, regulate the pH of the system to 3±0.5 with concentrated sulfuric acid, add an acetonitrile solution containing 3.9 kg (1 eq) of (4S,5S)-2,2,5-trimethyl-5-(2-azidoacetyl)-1,3-dioxolane

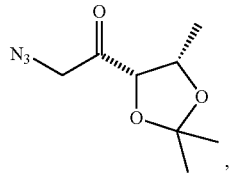

react at 27±5° C. for 8.5 hours, perform suction filtration and concentration to obtain 2.3 kg of (3S,4S)-1-amino-3,4-dihydroxy-2-pentanone

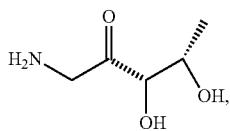

with a yield of 89%;

Step 8: add 23 L (10 ml/g) of propanol, 6.9 L (3 ml/g) of pure water, 0.9 kg of (0.3 eq) of potassium iodide, 4.8 kg (1.2 eq) of compound A (2-amino-6-chloro-5-nitro-3H-pyrimidin-4-one), 2.3 kg (1 eq) of (3S,4S)-1-amino-3,4-dihydroxy-2-pentanone

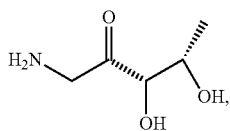

and 10.5 kg (6 eq) of diisopropylamine to a 50 L reaction bottle, react the system for 7 hours while preserving the temperature at 72±5° C., then add a potassium dihydrogen phosphate-dipotassium phosphate aqueous solution to regulate the pH of the system to 7.5±0.5; and filter the system to obtain 2.5 kg of 2-acetylamino-5-nitro-6-((3S,4S)-3,3-dihydroxy-2-oxo-pentylamino)-pyrimidin-4-one

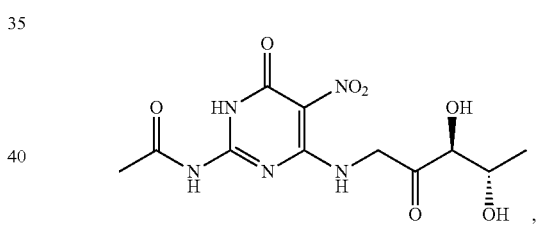

with a yield of 44%;

Step 9: add 1.25 kg (1 eq) of 2-acetylamino-5-nitro-6((3S,4S)-3,3-dihydroxy-2-oxo-pentylamino)-pyrimidin-4-one

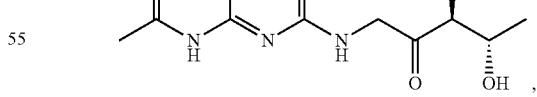

50 L (40 ml/g) of ethanol and 0.5 kg (0.4 g/g) of 10% palladium on carbon to a 100 L autoclave, introduce hydrogen until the reaction system pressure is 0.8±0.05 MPa, control the temperature of the system at 27±5° C. and the pressure at 0.8±0.05 MPa, react for 24 hours, filter the system, and regulate the pH to 11±0.5 to obtain an ethanol solution containing 1.1 kg of acetylamino-7,8-dihydropteridine

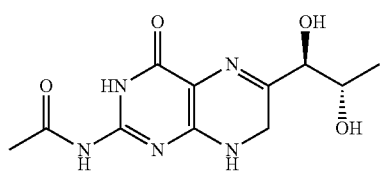 [SMILES: CC(=O)Nc1nc2c(c(=O)[nH]1)N=C([C@@H](O)[C@H](C)O)CN2]

which is used directly in the next step;

Step 10: add 0.44 kg (0.4 g/g) of palladium 10% on carbon in the presence of the ethanol solution containing 1.1 kg of acetylamino-7,8-dihydropteridine

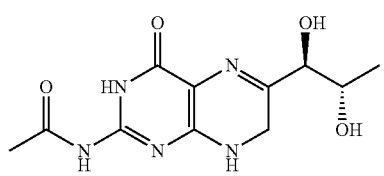 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.8±0.05 MPa, control the temperature of the system at 25±5° C. and the pressure at 0.8±0.05 MPa, react for 80 hours, after reacting thoroughly, perform quenching in 20 kg (8 eq) of dilute hydrochloric acid having a concentration of 15%, and perform suction filtration and drying to the system to obtain a target product, i.e. a crude product of sapropterin dihydrochloride

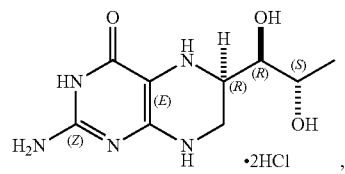

recrystallize and purify the crude product by 21.4 L (20 ml/g) of ethanol at 35±5° C. to obtain 0.4 kg of a pure product, with a yield of 46.2%, a purity of 98.5% and an enantiomeric excess of 99.2%.

Embodiment 6: main raw material:

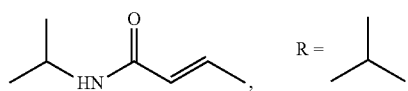

and X=N

Step 1: add 522 kg (0.05 eq) of a tetrahydrofuran solution containing a samarium catalyst having a concentration of 2%, 9.1 kg (0.05 eq) of (R)-(+)-1,1'-bi-2-naphthol, 8.9 kg (0.05 eq) of triphenylphosphine oxide, and 567 kg (7 kg/kg) of a 4 A molecular sieve to a 3000 L reaction kettle, after stirring uniformly, control the system temperature at 8±5° C., add 57.4 kg (0.eq) of a tert-butyl hydroperoxide toluene solution having a concentration of 50%, add 81.1 kg (1 eq) of (E)-N-isopropylbut-2-enamide

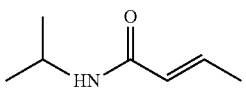

to the system after adding the tert-butyl hydroperoxide toluene solution, react for 34 hours while preserving the temperature, add 6.1 kg (0.05 eq) of citric acid to the system to stop the reaction, and perform centrifugation, concentration and rectification to the system to obtain 56.1 kg of (2S,3R)-2,3-epoxy-diisopropylamido butyrate

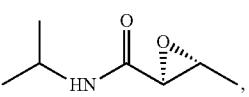

with a yield of 61.5%;

Step 2: add 11.4 kg (0.5 eq) of acetone, and 8.8 kg (0.1 eq) of zinc bromide to a 500 L enamel vessel, control the temperature at 20±5° C., add 56.1 kg (1 eq) of (2S,3R)-2,3-epoxy-diisopropylamido butyrate

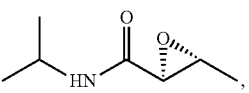

react for 8.5 hours while preserving the temperature, add 329 kg (2 eq) of a sodium bicarbonate aqueous solution having a concentration of 10%, and perform liquid separation, extraction and concentration to the system to obtain 64.7 kg of (4S,5S)-2,2,5-trimethyl-2,3-acetonide-diisopropylamido butyrate

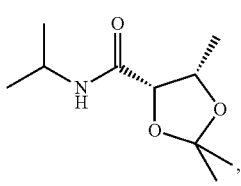

with a yield of 82%;

Step 3: add 259 L (4 ml/g) of tetrahydrofuran, and 64.7 kg (1 eq) of (4S,5S)-2,2,5-trimethyl-2,3-acetonide-diisopropylamido butyrate

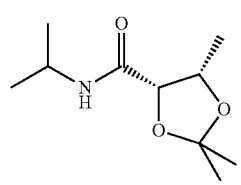

to a 1000 L reaction kettle, increase the temperature to 27±5° C., add 2.9 kg (0.5 eq) of pure water and 29.9 kg (0.5 eq) of a methanol solution of sodium methoxide having a concentration of 29.9%, react for 4 hours while preserving the temperature, perform centrifugation, dissolve a filter cake in 194 L (3 ml/g) of tetrahydrofuran, add 39 kg (1 eq) of L-α-phenylethylamine, preserve the temperature at 18±5° C. for 3.5 hours, and perform centrifugation and drying to obtain 54.3 kg of 1-phenyltehanamine (4S,5S)-2,2,5-trimethyl-1,3-dioxolane-4-carboxylate

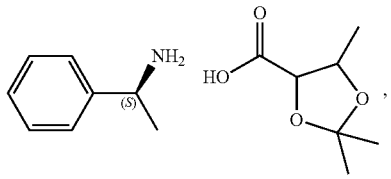

with a yield of 60%;

Step 4: add 30 L (3 ml/g) of 2-methyltetrahydrofuran, 10 kg (1 eq) of 1-phenyltehanamine (4S,5S)-2,2,5-trimethyl-1,3-dioxolane-4-carboxylate

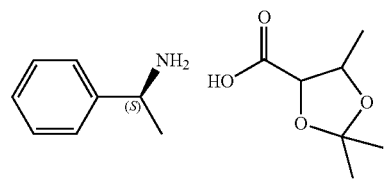

to a 72 L reaction bottle, then add a dilute phosphoric acid aqueous solution having a concentration of 10% to the system to regulate the pH at 1.5±0.5, control the temperature at −5±5° C., react for 1 hour, perform liquid separation to obtain an organic phase, add 3.7 kg of (0.8 eq) N,N-diisopropylethylamine to the organic phase, and concentrate the system to obtain 5.3 kg of (4S,5S)-2,2,5-trimethyl-1,3-dioxolan-4-methanoic acid

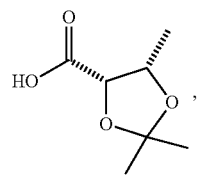

with a yield of 92.5%;

Step 5: add 42 L (8 ml/g) of 1,4-dioxane, 5.3 kg of 1,3-dioxolan-4-methanoic acid

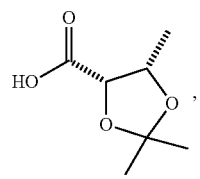

and 8.5 kg (2 eq) of N,N-diisopropylethylamine to a 100 L reaction bottle, reduce the temperature to −10±5° C., add 4 kg (21.0 eq) of propyl chloroformate, react for 2 hours while preserving the temperature, introduce a diazomethane gas for 2 hours, add 12 kg (2 eq) of a hydrochloride ethanol solution having a concentration of 20%, react for 2 hours, add sodium hydroxide to regulate the pH value to 7.5±0.5, and perform extraction, liquid separation and concentration to obtain 5.1 kg of (4S,5S)-2,2,5-trimethyl-5-chloroacetyl-1,3-dioxolane

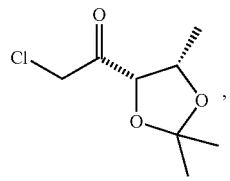

with a yield of 81%; Step 6: add 41 L (8 ml/g) of tetrahydrofuran, 5.1 kg of (4S,5S)-2,2,5-trimethyl-5-chloroacetyl-1,3-dioxolane

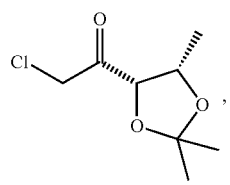

3.1 kg (1 eq) of azidotrimethylsilane, and 0.5 kg (0.1 eq) of sodium iodide to a 72 L bottle, react the system for 30 hours while preserving the temperature at 12±5° C., perform filtering and concentration to obtain an acetone solution containing 4.6 kg of (4S,5S)-2,2,5-trimethyl-5-(2-azidoacetyl)-1,3-dioxolane

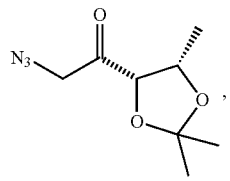

with a yield of 87.5%;

Step 7: add 28 L (6 ml/g) of 1,4-dioxane and 0.23 kg (0.05 g/g) of palladium 10% on carbon to a 50 L reaction kettle, introduce hydrogen until the system pressure is 0.8±0.1 MPa, regulate the pH of the system to 3±0.5 with acetic acid, add an acetonitrile solution containing 4.6 kg (1 eq) of (4S,5S)-2,2,5-trimethyl-5-(2-azidoacetyl)-1,3-dioxolane

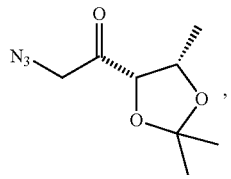

react at 27±5° C. for 8.5 hours, react for 8.5 hours, perform suction filtration and concentration to obtain 2.7 kg of (3S,4S)-1-amino-3,4-dihydroxy-2-pentanone

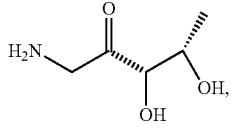

with a yield of 87.7%;

Step 8: add 16.3 L (6 ml/g) of isopropanol, 2.7 L (1 g/g) of pure water, 0.4 kg of (0.1 eq) of sodium iodide, 4.8 kg (1.0 eq) of compound A (2-amino-6-chloro-5-nitro-3H-pyrimidin-4-one), 2.7 kg (1 eq) of (3S,4S)-1-amino-3,4-dihydroxy-2-pentanone

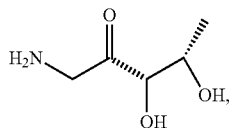

and 8.7 kg (4 eq) of sodium carbonate to a 50 L reaction bottle, react the system for 7 hours while preserving the temperature at 45±5° C., then add an ammonium formate-ammonia aqueous solution to regulate the pH of the system to 6.5±0.5; and filter the system to obtain 2.85 kg of 2-acetylamino-5-nitro-6((3S,4S)-3,3-dihydroxy-2-oxo-pentylamino)-pyrimidin-4-one

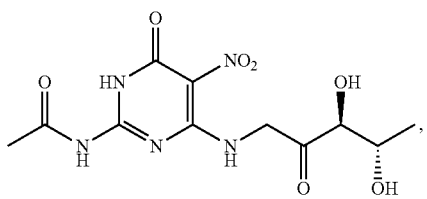 [SMILES: CC(=O)Nc1nc(NCC(=O)[C@@H](O)[C@H](C)O)c([N+](=O)[O-])c(=O)[nH]1]

with a yield of 42.5%;

Step 9: add 2 kg (1 eq) of 2-acetylamino-5-nitro-6-((3S,4S)-3,3-dihydroxy-2-oxo-pentylamino)-pyrimidin-4-one

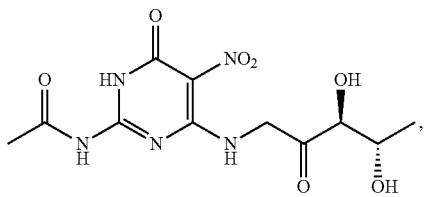 [SMILES: CC(=O)Nc1nc(NCC(=O)[C@@H](O)[C@H](C)O)c([N+](=O)[O-])c(=O)[nH]1]

60 L (30 ml/g) of ethanol and 0.2 kg (0.1 g/g) of platinum dioxide to a 100 L autoclave, introduce hydrogen until the reaction system pressure is 0.6±0.05 MPa, control the temperature of the system at 20±5° C. and the pressure at 0.6±0.05 MPa, react for 20 hours, filter the system, and regulate the pH to 11±0.5 to obtain an ethanol solution containing 1.7 kg of acetylamino-7,8-dihydropteridine

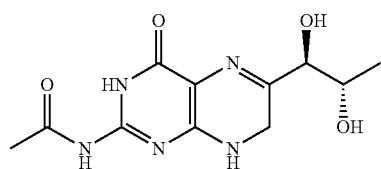 [SMILES: CC(=O)Nc1nc2c(c(=O)[nH]1)N=C([C@@H](O)[C@H](C)O)CN2]

which is used directly in the next step;

Step 10: add 0.2 kg (0.1 g/g) of platinum dioxide in the presence of the ethanol solution containing 1.7 kg of acetylamino-7,8-dihydropteridine

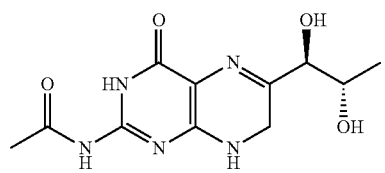 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.6±0.05 MPa, control the temperature of the system at 15±5° C. and the pressure at 0.6±0.05 MPa, react for 75 hours, after reacting thoroughly, perform quenching in 30 kg (5 eq) of dilute hydrochloric acid having a concentration of 10%, and perform suction filtration and drying to the system to obtain a target product, i.e. a crude product of sapropterin dihydrochloride

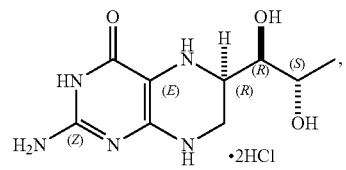

recrystallize and purify the crude product by 17 L (10 ml/g) of butanone at 15±5° C. to obtain 0.6 kg of a pure product, with a yield of 43%, a purity of 98.4% and an enantiomeric excess of 98.9%.

Thus, it can be seen that synthesis of a sapropterin dihydrochloride compound and an intermediate thereof disclosed in a method of the present disclosure can obtain a target product with a high purity, a high enantiomeric excess, and a high yield. The synthesis method uses readily-available raw materials, significantly reduces a synthesis route of sapropterin dihydrochloride. The technological conditions are stable, and there is less pollution in the whole operation process, hence providing an effective scheme for mass industrial production of sapropterin dihydrochloride.

The above are only preferred embodiments of the present disclosure and should not be used to limit the present disclosure. For those skilled in the art, the present disclosure may have various modifications and changes. Any modifications, equivalent replacements, improvements and the like within the spirit and principle of the present disclosure shall fall within the scope of protection of the present disclosure.

What is claimed is:

1. A method for synthesizing sapropterin dihydrochloride, wherein it comprises the following specific steps:

Step 1: adding (R)-(+)-1,1'-bi-2-naphthol, triphenylphosphine oxide and a 4 A molecular sieve in the presence of a tetrahydrofuran solution of a samarium catalyst having a concentration of 5% to 10%, after stirring uniformly, controlling the system temperature at 0° C. to 25° C., adding an oxidant, and adding a main raw material compound 1

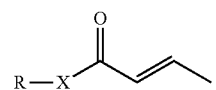

to the system after adding the oxidant, where X=NH or O, R=C1 to C6 alkyl or benzyl, reacting for 20 to 36 hours while maintaining the temperature, then adding citric acid to the system to stop the reaction, and performing centrifugation, concentration and rectification to obtain compound 2 having a structural formula of

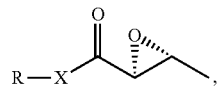

when X is NH, compound 1 is alkyl crotonate, and compound 2 is (2S,3R)-2,3 epoxy-alkylamide butyrate; when X is oxygen, compound 1 is alkyl crotonate or benzyl crotonate and compound 2 is (2S,3R)-2,3 epoxy-alkylbutyrate or (2S,3R)-2,3 epoxy-benzyl butyrate, wherein the molar ratio of

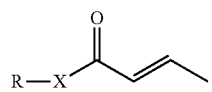

to the samarium catalyst is 1:0.05 to 0.5, the molar ratio of

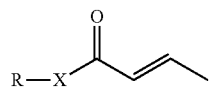

to (R)-(+)-1,1'-bi-2-naphthol is 1:0.05 to 0.5, the molar ratio of

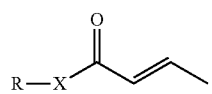

to triphenylphosphine oxide is 1:0.05 to 0.5, the mass ratio of

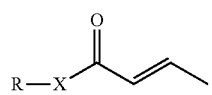

to the 4 A molecular sieve is 1:5 to 15, the molar ratio of

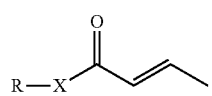

to the oxidant is 1:0.5 to 3, and the molar ratio of

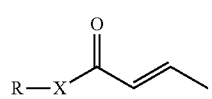

to citric acid is 1:0.05 to 0.5;

Step 2: adding a Lewis acid in the presence of acetone, controlling the temperature at 10° C. to 30° C., adding compound 2, reacting for 5 to 10 hours while maintaining the temperature, adding an inorganic base aqueous solution having a concentration of 5% to 10% to the system, and performing liquid separation, extraction and concentration to the system to obtain compound 3 having a structural formula of

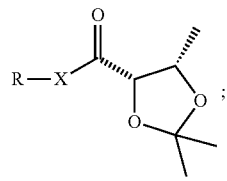

when X is NH, compound 3 is (4S,5S)-2,3-acetonide-alkylbutyramide or (4S,5S)-2,3-acetonide-benzylbutyramide; when X is oxygen, compound 3 is (4S,5S)-2,3-acetonide-alkylbutyrate or (4S,5S)-2,3-acetonide-benzyl butyrate;

wherein the molar ratio of compound 2 to acetone is 1:1 to 4; the molar ratio of compound 2 to the Lewis acid is 1:0.1 to 1; and the molar ratio of compound 2 to the inorganic base is 1:0.5 to 3;

Step 3: adding compound 3 in the presence of a polar solvent, increasing the temperature to 25° C. to 40° C., adding pure water and an alkaline solution, reacting for 3 to 8 hours while maintaining the temperature, performing centrifugation, dissolving a filter cake in a polar solvent which is the same as the reaction polar solvent, adding a resolving reagent, maintaining the temperature at 15° C. to 30° C. for 3 to 5 hours, performing centrifugation and drying to obtain compound 4, i.e. 1-phenylalkylamine (4S,5S)-2,2,5-trimethyl-1,3-dioxolane-4-carboxylate having a structural formula of

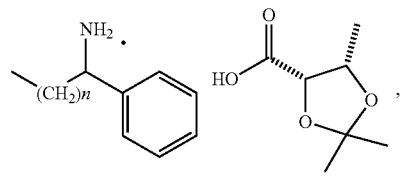

where n=0, 1;

wherein the concentration of the use amount of compound 3 to that of the reaction polar solvent is 1 g/3 to 10 ml; the molar ratio of compound 3 to pure water is 1:0.5 to 3; the molar ratio of compound 3 to an alkaline substance in the alkaline solution is 1:0.5 to 2; the concentration of the use amount of compound 3 to that of the polar solvent for dissolving the filter cake is 1 g/2 to 10 ml; the molar ratio of compound 3 to the resolving reagent is 1:1 to 5;

Step 4: adding compound 4 in the presence of an ether solvent, then adding an inorganic acid aqueous solution having a concentration of 5% to 10% to the system to regulate the pH to 1 to 3, controlling the temperature at −10° C. to 10° C., maintaining the temperature for 1 hour, performing liquid separation to obtain an organic phase, adding N,N-diisopropylethylamine to the organic phase, and concentrating the system to obtain compound 5, i.e. (4S,5S)-2,2,5-trimethyl 1,3-dioxolan-4-methanoic acid having a structural formula of

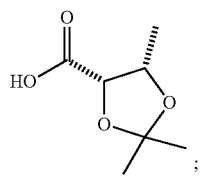

wherein the concentration of the use amount of compound 4 to that of the ether solvent is 1 g/3 to 10 ml and the molar ratio of compound 4 to N,N-diisopropylethylamine is 1:0.8 to 3;

Step 5: adding compound 5 and N,N-diisopropylethylamine in the presence of an ether solvent, reducing the temperature to −30° C. to 0° C., adding a chloroformate, reacting for 1 to 2 hours while maintaining the temperature, introducing a diazomethane gas for 1 to 2 hours, adding a hydrochloride ethanol solution, reacting for 1 to 2 hours, adding an alkaline reagent to regulate the pH value to 7 to 9, performing extraction, liquid separation and concentration to obtain compound 6, i.e. (4S,5S)-2,2,5-trimethyl-5-chloroacetyl-1,3-dioxolane having a structural formula of

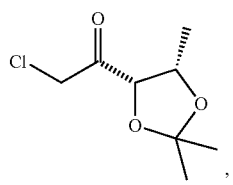

wherein the concentration of the use amount of compound 5 to that of the ether solvent is 1 g/5 to 15 ml; the molar ratio of compound 5 to N,N-diisopropylethylamine is 1:1 to 5; the molar ratio of compound 5 to the chloroformate is 1:1 to 3; and the molar ratio of compound 5 to hydrogen chloride in the hydrochloride ethanol solution is 1:1 to 5;

Step 6: adding compound 6, a trinitride and a catalyst in the presence of a polar solvent, reacting the system at 15° C. to 40° C. for 20 to 30 hours while maintaining the temperature, then performing filtering and concentration to obtain a solution of compound 7 which is used directly in the next step; compound 7 is (4S,5S)-2,2,5-trimethyl-5-(2-azidoacetyl)-1,3-dioxolane having a structural formula of

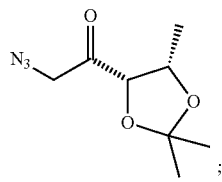

wherein the concentration of the use amount of compound 6 to that of the polar solvent is 1 g/5 to 15 ml; the molar ratio of compound 6 to the trinitride is 1:1 to 4; and the molar ratio of compound 6 to the catalyst is 1:0.05 to 0.8;

Step 7: adding triphenylphosphine and water, or palladium on carbon and hydrogen, or Raney nickel and hydrogen in the presence of an ether solvent, regulating the pH of the system to 1 to 4 with an acid reagent, adding a solution of compound 7, maintaining the temperature at 10° C. to 30° C., reacting for 5 to 10 hours, performing suction filtration and concentration to obtain a filtrate containing compound 8, the filtrate being used directly in the next step or a solid of compound 8 being separated from the filtrate for use in the next step; the compound 8 is (3S,4S)-1-amino-3,4-dihydroxy-2-pentanone having a structural formula of

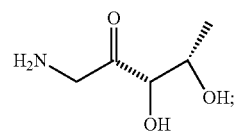

wherein the concentration of the use amount of compound 7 to that of the ether solvent is 1 g/5 to 15 ml; the molar ratio of compound 7 to triphenylphosphine is 1:0.1 to 3; the ratio of the use amount of compound 7 to that of water is 1:0.1 to 3; the mass ratio of compound 7 to 5% palladium on carbon or 10% palladium on carbon or Raney nickel is 1:0.05 to 0.6; the hydrogen is introduced until the pressure of the system is 0.4 to 0.9 MPa;

Step 8: adding a catalyst, compound A, i.e. 2-amino-6-chloro-5-nitro-3H-pyrimidin-4-one having a structural formula of

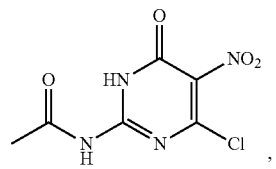

compound 8, and an alkaline reagent in the presence of an alcoholic solvent and pure water, reacting the system at 30° C. to 80° C. for 4 to 8 hours while maintaining the temperature, adding a buffer solution to regulate the pH of the system to 6 to 8, and filtering the system to obtain compound 9, i.e. 2-acetylamino-5-nitro-6-((3S,4S)-3,3-dihydroxy-2-oxopentylamino)-pyrimidin-4-one

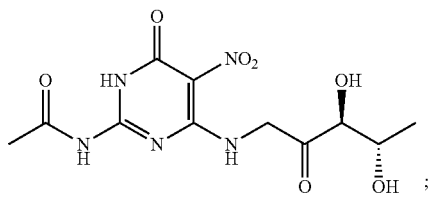 [SMILES: CC(=O)Nc1nc(NCC(=O)[C@@H](O)[C@H](C)O)c([N+](=O)[O-])c(=O)[nH]1]

having a structural formula of
wherein the concentration of the use amount of compound 8 to that of the alcoholic solvent is 1 g/5 to 15 ml; the concentration of the use amount of compound 8 to that of pure water is 1 g/1 to 5 ml; the molar ratio of compound 8 to compound A is 1:1 to 1.5; the molar ratio of compound 8 to the catalyst is 1:0.05 to 0.5; and the molar ratio of compound 8 to the alkaline reagent is 1:3 to 8;

Step 9: adding a catalyst in the presence of compound 9 and a polar solvent, introducing hydrogen until the pressure of the system is 0.4 to 0.9 MPa, controlling the temperature of the system at 15° C. to 30° C. and the pressure at 0.4 to 0.9 MPa, reacting for 18 to 24 hours, filtering the system, and regulating the pH of the system to 11 to 12 with an alkaline reagent to obtain a solution of compound 10 to be used directly in the next step, compound 10 is acetylamino-7,8-dihydropteridine having a structural formula of

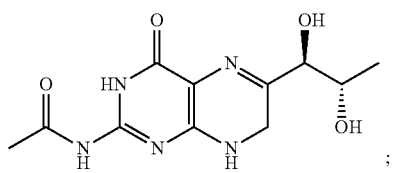 [SMILES: CC(=O)Nc1nc2c(c(=O)[nH]1)N=C([C@@H](O)[C@H](C)O)CN2]

wherein the concentration of the use amount of compound 9 to that of the polar solvent is 1 g/20 to 50 ml and the mass ratio of compound 9 to the catalyst is 1:0.05 to 0.6;

Step 10: adding a catalyst in the presence of the solution of the compound 10 obtained in Step 9, introducing hydrogen until the pressure of the system is 0.4 to 0.9 MPa, controlling the temperature of the system at 10° C. to 30° C., controlling the pressure at 0.4 to 0.9 MPa, reacting for 72 to 84 hours, performing quenching in dilute hydrochloric acid having a concentration of 10% to 20% after reacting thoroughly, and performing suction filtration and drying to the system to obtain compound 11, i.e. a target product, a sapropterin dihydrochloride crude product, and further crystallizing and purifying the sapropterin dihydrochloride crude product with an alcoholic solvent or a ketone solvent at 0° C. to 40° C. to obtain a sapropterin dihydrochloride pure product, wherein the mass ratio of compound 10 to the catalyst is 1:0.05 to 0.6; the molar ratio of compound 10 to hydrochloric acid is 1:3 to 10; and the concentration of the use amount of compound 10 to that of the alcoholic solvent or the ketone solvent is 1 g/5 to 25 ml.

2. A method for synthesizing sapropterin dihydrochloride according to claim 1, wherein the oxidant in Step 1 is N-bromobutanimide, meta-chloroperoxybenzoic acid, hydrogen peroxide having a concentration of 35% or a toluene solution of tert-butyl hydroperoxide having a concentration of 50%; the molar ratio of

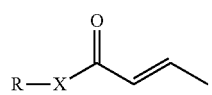

to the samarium catalyst is 1:0.05 to 0.4; the molar ratio of

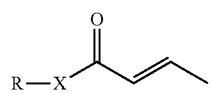

to (R)-(+)-1,1'-bi-2-naphthol is 1:0.05 to 0.4; the molar ratio of

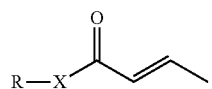

to triphenylphosphine oxide is 1:0.05 to 0.4; the mass ratio of

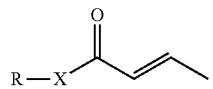

to the 4 A molecular sieve is 1:6 to 12; the molar ratio of

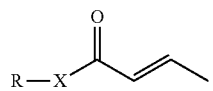

to the oxidant is 1:0.5 to 2.5 and the molar ratio of

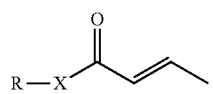

to citric acid is 1:0.05 to 0.4.

3. A method for synthesizing sapropterin dihydrochloride according to claim 1, wherein in Step 2, the Lewis acid is aluminium chloride, ferric chloride, zinc chloride, a boron trifluoride diethyletherate solution, zinc bromide, or lithium chloride; the inorganic base is sodium bicarbonate, sodium carbonate, sodium hydroxide, potassium hydroxide, potassium carbonate or potassium bicarbonate; the ratio of the use amount of compound 2 to that of acetone is 1:1 to 3.5; the ratio of the use amount of compound 2 to that of the Lewis acid is 1:0.1 to 0.8; the ratio of the use amount of compound 2 to that of the inorganic base is 1:0.5 to 2.5.

4. A method for synthesizing sapropterin dihydrochloride according to claim 1, wherein in Step 3, the polar solvent is tetrahydrofuran, methanol or ethanol; the resolving reagent is L-α-phenylethylamine or L-α-amphetamine; the alkaline solution is a methanol solution of sodium methoxide having a concentration of 29%, a potassium hydroxide aqueous solution having a concentration of 20% or a sodium hydroxide aqueous solution having a concentration of 20%; the concentration of the use amount of compound 3 to that of the reaction polar solvent is 1 g/3 to 8 ml; the molar ratio of compound 3 to pure water is 1:0.5 to 1.8; the molar ratio of compound 3 to the alkaline substance in the alkaline solution is 1:0.5 to 1.8; the concentration of the use amount of compound 3 to that of the polar solvent for dissolving the filter cake is 1 g/3 to 8 ml; the molar ratio of compound 3 to the resolving reagent is 1:1 to 4.

5. A method for synthesizing sapropterin dihydrochloride according to claim 1, wherein in Step 4, the ether solvent is tetrahydrofuran, 2-methyltetrahydrofuran, methyl tert-butyl ether, 1,4-dioxane or ether; the inorganic acid is sulphuric acid, hydrochloric acid or phosphoric acid; the concentration of the use amount of compound 4 to that of the ether solvent is 1 g/3 to 8 ml; and the molar ratio of compound 4 to N,N-diisopropylethylamine is 1:0.8 to 2.5.

6. A method for synthesizing sapropterin dihydrochloride according to claim 1, wherein in Step 5, the ether solvent is tetrahydrofuran, 2-methyltetrahydrofuran, methyl tert-butyl ether, 1,4-dioxane or ether; the chloroformate is methyl chloroformate, ethyl chloroformate, or propyl chloroformate; the alkaline reagent is triethylamine, sodium carbonate, potassium carbonate, sodium bicarbonate, potassium bicarbonate, sodium hydroxide or potassium hydroxide; the concentration of the use amount of compound 5 to that of the ether solvent is 1 g/6 to 12 ml; the molar ratio of compound 5 to N,N-diisopropylethylamine is 1:1.5 to 4; the molar ratio of compound 5 to the chloroformate is 1:1 to 2.5; and the molar ratio of compound 5 to hydrogen chloride in the hydrochloride ethanol solution is 1:1.5 to 4.5.

7. A method for synthesizing sapropterin dihydrochloride according to claim 1, wherein in Step 6, the polar solvent is acetonitrile, methanol, ethanol, acetone or tetrahydrofuran; the catalyst is sodium iodide or potassium iodide; the trinitride is sodium azide or azidotrimethylsilane; the concentration of the use amount of compound 6 to that of the polar solvent is 1 g/6 to 12 ml; the molar ratio of compound 6 to the trinitride is 1:1 to 3; and the molar ratio of compound 6 to the catalyst is 1:0.05 to 0.6.

8. A method for synthesizing sapropterin dihydrochloride according to claim 1, wherein in Step 7, the ether solvent is tetrahydrofuran, 2-methyltetrahydrofuran, methyl tert-butyl ether, 1,4-dioxane or ether; the acid reagent is citric acid, p-toluenesulfonic acid, benzenesulfonic acid, formic acid, acetic acid, hydrochloric acid, sulfuric acid or phosphoric acid; the concentration of the use amount of compound 7 to that of the ether solvent is 1 g/5 to 12 ml; the molar ratio of compound 7 to triphenylphosphine is 1:0.6 to 2; the ratio of the use amount of compound 7 to that of water is 1:0.6 to 2; the mass ratio of compound 7 to 5% palladium on carbon or 10% palladium on carbon or Raney nickel is 1:0.05 to 0.4; the hydrogen is introduced until the pressure of the system is 0.5 to 0.8 MPa.

9. A method for synthesizing sapropterin dihydrochloride according to claim 1, wherein in Step 8, the alcoholic solvent is methanol, ethanol, propanol or isopropanol; the catalyst is sodium iodide or potassium iodide; the alkaline reagent is triethylamine, diisopropylethylamine, diisopropylamine, pyridine, sodium bicarbonate, potassium bicarbonate, sodium carbonate, potassium carbonate or cesium carbonate; the buffer solution is a sodium dihydrogen phosphate-disodium hydrogen phosphate aqueous solution, a potassium dihydrogen phosphate-dipotassium hydrogen phosphate aqueous solution or an ammonium formate-ammonia aqueous solution; the concentration of the use amount of compound 8 to that of the alcoholic solvent is 1 g/6 to 12 ml; the concentration of the use amount of compound 8 to that of pure water is 1 g/1 to 4 ml; the molar ratio of compound 8 to compound A is 1:1 to 1.4; the molar ratio of compound 8 to the catalyst is 1:0.1 to 0.4; and the molar ratio of compound 8 to the alkaline reagent is 1:4 to 7.

10. A method for synthesizing sapropterin dihydrochloride according to claim 1, wherein in Step 9, the catalyst is Raney nickel, 5% palladium on carbon, 10% palladium on carbon, platinum dioxide or 20% palladium on carbon; the polar solvent is pure water, methanol or ethanol; the alkaline solution is sodium hydroxide, potassium hydroxide, sodium carbonate or potassium carbonate; the concentration of the use amount of compound 9 to that of the polar solvent is 1 g/25 to 45 ml and the mass ratio of compound 9 to the catalyst is 1:0.05 to 0.5.

11. A method for synthesizing sapropterin dihydrochloride according to claim 1, wherein in Step 10, the catalyst is Raney nickel, 5% palladium on carbon, 10% palladium on carbon, platinum dioxide or 20% palladiumon carbon; the alcoholic solvent is methanol, ethanol, isopropanol or n-butanol, ethanol or isopropanol, optimally methanol; the ketone solvent is acetone or butanone;

the mass ratio of compound 10 to the catalyst is 1:0.05 to 0.5; the molar ratio of compound 10 to hydrochloric acid is 1:4 to 9; and the concentration of the use amount of compound 10 to that of the alcoholic solvent or the ketone solvent is 1 g/5 to 20 ml.

\* \* \* \* \*